United States Patent [19]
Feldman et al.

[11] Patent Number: 5,665,754
[45] Date of Patent: Sep. 9, 1997

[54] SUBSTITUTED PYRROLIDINES

[75] Inventors: Paul Lawrence Feldman, Durham; Jeffrey Alan Stafford, Cary, both of N.C.

[73] Assignee: Glaxo Wellcome Inc., Research Triangle Park, N.C.

[21] Appl. No.: 123,837

[22] Filed: Sep. 20, 1993

[51] Int. Cl.$^6$ .................... A61K 31/40; C07D 207/09
[52] U.S. Cl. .................. 514/397; 514/423; 548/314.7; 548/531; 548/536; 548/538; 548/542
[58] Field of Search ..................... 514/397, 423; 548/314.7, 531, 536, 538, 542

[56] References Cited

U.S. PATENT DOCUMENTS

| | | | |
|---|---|---|---|
| 4,012,495 | 3/1977 | Schmiechen et al. | 424/274 |
| 4,219,560 | 8/1980 | Houlihan | 424/267 |
| 4,960,457 | 10/1990 | Woolard | 71/95 |
| 5,068,245 | 11/1991 | Zipplies et al. | 514/429 |
| 5,068,246 | 11/1991 | Zipplies et al. | 514/429 |
| 5,270,328 | 12/1993 | Cantrell et al. | 514/331 |

FOREIGN PATENT DOCUMENTS

| | | |
|---|---|---|
| 748392 | 4/1969 | Belgium . |
| 748393 | 4/1969 | Belgium . |
| 770308 | 7/1970 | Belgium . |
| 804701 | 9/1972 | Belgium . |
| 826923 | 3/1974 | Belgium . |
| 846335 | 9/1975 | Belgium . |
| 2807623 | 2/1977 | Denmark . |
| 3104435 | 2/1981 | Denmark . |
| 3253 | 12/1977 | European Pat. Off. . |
| 21772 | 7/1979 | European Pat. Off. . |
| 164853A | 5/1984 | European Pat. Off. . |
| 309913A | 9/1987 | European Pat. Off. . |
| 309914 | 9/1987 | European Pat. Off. . |
| 381235 | 2/1989 | European Pat. Off. . |
| 439766 | 1/1990 | European Pat. Off. . |
| 470805A1 | 8/1991 | European Pat. Off. . |
| 511865A1 | 4/1992 | European Pat. Off. . |
| 74016872 | 5/1970 | Japan . |
| 51082258 | 4/1974 | Japan . |
| 52-156859 | 6/1976 | Japan . |
| 1298204 | 11/1985 | U.S.S.R. . |
| 2027025 | 8/1978 | United Kingdom . |
| WO87/06576 | 11/1987 | WIPO . |
| WO91/16303 | 10/1991 | WIPO . |
| WO92/00968 | 1/1992 | WIPO . |
| WO92/02220 | 2/1992 | WIPO . |
| WO92/07567 | 5/1992 | WIPO . |
| WO92/12961 | 8/1992 | WIPO . |
| WO92/19594 | 11/1992 | WIPO . |
| WO93/07111 | 4/1993 | WIPO . |
| WO93/07141 | 4/1993 | WIPO . |
| WO93/07146 | 4/1993 | WIPO . |
| WO95/08534 | 3/1995 | WIPO . |

OTHER PUBLICATIONS

H. Yuki and M. Yatabe, "Pyrroles and Other 5-Membered Rings," *Chemical Abstracts*, abstract No. 72427, vol. 86, No. 11, p. 594, Mar. 1977.

S. Denmark and L. Marcin, "Nitroalkene [4+2] Cycloaddition as a General and Stereoselective Route to the Synthesis of 3,3-and 3,4-Disubstituted Pyrrolidines," *J. Org. Chem.*, vol. 58, No. 25, pp. 3857-3868 (1993).

M. Marivet, et al., "Inhibition of Cyclic Adenosine-3', 5'-monophosphate Phosphodiesterase from Vascular Smooth Muscle by Rolipram Analogues," *J. Med. Chem.*, vol. 32, No. 7, pp. 1450–1457, 1 1989.

*Primary Examiner*—Jacqueline Haley
*Attorney, Agent, or Firm*—Charles E. Dadswell

[57] ABSTRACT

Novel pyrrolidine compounds which are useful for inhibiting the function of Type IV phosphodiesterase (PDE-IV) as well as methods for making the same are disclosed. Applications in treating inflammatory diseases and other diseases involving elevated levels of cytokines, as well as central nervous system (CNS) disorders, are also disclosed.

26 Claims, 3 Drawing Sheets

SUBSTITUTED PYRROLIDINES

FIELD OF INVENTION

The present invention relates to novel pyrrolidine compounds which are useful for inhibiting the function of Type IV phosphodiesterase (PDE-IV) as well as methods for making the same and their applications in treating inflammatory diseases and other diseases involving elevated levels of cytokines, as well as central nervous system (CNS) disorders.

BACKGROUND OF THE INVENTION

Sites of chronic inflammation are characterized by the presence and activation of multiple types of inflammatory cells, particularly cells of lymphoid lineage (including T lymphocytes) and myeloid lineage (including granulocytes, macrophages and monocytes). Pro-inflammatory mediators, including cytokines such as tumor necrosis factor (TNF) and interleukin-1 (IL-1), are produced by these activated cells. Accordingly, an agent which suppresses the activation of these cells or their production of pro-inflammatory cytokines would be useful in the therapeutic treatment of inflammatory diseases or other diseases involving elevated levels of cytokines.

Cyclic AMP (adenosine monophosphate) has been shown to be a second messenger which mediates the biologic responses of cells to a wide range of extracellular stimuli. When the appropriate agonist binds to specific cell surface receptors, adenylate cyclase is activated to convert ATP (adenosine triphosphate) to cAMP. The actions of cAMP are terminated by cyclic nucleotide phosphodiesterases (PDEs) which hydrolyze the 3'-phosphodiesterase bond to form 5'-AMP, an inactive metabolite. In short, the intracellular enzyme family of PDEs regulates the level of cAMP in cells. Accordingly, the inhibition of PDE function would prevent the conversion of cAMP to the inactive metabolite 5'-AMP and, consequently, maintain higher cAMP levels (see Beavo and Houslay, Cyclic Nucleotide Phosphodiesterases: Structure, Regulation and Drug Action, Wiley, Chichester, pgs 3–14, 1990).

Elevated levels of cAMP in human myeloid and lymphoid lineage cells are associated with the suppression of cell activation. Type IV cAMP phosphodiesterase (PDE-IV) is a predominant PDE isotype in these cells and is thus a major mechanism of cAMP degradation. It is now recognized that inhibiting PDE-IV function can cause elevation of cAMP in these cells and suppression of cell activation (for review, see Torphy, et al, Novel phosphodiesterase inhibitors for the therapy of asthma, Drug News and Perspectives 6:203–214; Giembycz and Dent, Prospects for selective cyclic nucleotide phosphodiesterase inhibitors in the treatment of bronchial asthma, Clin Exp Allergy 22:337–344).

In particular, PDE-IV inhibitors have been shown to inhibit production of TNFα and partially inhibit IL-1β release by monocytes (see Semmler, et al, The specific type-IV phosphodiesterase inhibitor rolipram suppresses TNFα production by human mononuclear cells, Int J Immunopharmacol 15:409–413, 1993; Molnar-Kimber, et al, Differential regulation of TNF-α and IL-1β production from endotoxin stimulated human monocytes by phosphodiesterase inhibitors, Mediators of Inflammation 1:411–417, 1992). PDE-IV inhibitors have also been shown to inhibit the production of super oxide radicals from human polymorphonuclear leukocytes [see Verghese, et al, J Mol Cell Cardiol 12 (Suppl. II), sS.61; Nielson, et al, Effects of selective phosphodiesterase inhibitors on the polymorphonuclear leukocyte respiratory burst, J Allergy Clin Immunol 86:801–808, 1990]; to inhibit the release of vasoactive amines and prostanoids from human basophils (see Peachell, et. al., Preliminary identification and role of phosphodiesterase isozymes in human basophils, J Immunol 148:2503–2510, 1992); to inhibit respiratory bursts in eosinophils (see Dent, et el, Inhibition of eosinophil cyclic nucleotide PDE activity and opsonized zymosan stimulated respiratory burst by type IV-selective PDE inhibitors, Br J Pharmacol 103:1339–1346, 1991); and to inhibit the activation of human T-lymphocytes (see Robicsek, et. al., Multiple high-affinity cAMP-phosphodiesterases in human T-lymphocytes, Biochem Pharmacol 42:869–877, 1991).

Inflammatory cell activation and excessive or unregulated cytokine (e.g., TNFα and IL-1β) production are implicated in allergic, autoimmune or inflammatory diseases or disorders, such as rheumatoid arthritis, osteoarthritis, gouty arthritis, spondylitis, sepsis, septic shock, endotoxic shock, gram negative sepsis, gram positive sepsis, toxic shock syndrome, asthma, chronic bronchitis, allergic rhinitis, allergic conjunctivitis, vernal conjunctivitis, eosinophilic granuloma, adult respiratory distress syndrome, chronic pulmonary inflammatory disease, silicosis, pulmonary sarcoidosis, reperfusion injury of the myocardium, brain or extremities, fibrosis, cystic fibrosis, keloid formation, scar formation, atherosclerosis, transplant rejection disorders such as graft vs. host reaction and allograft rejection, chronic granulonephritis, lupus, inflammatory bowel disease such as Crohn's disease and ulcerative colitis and inflammatory dermatoses such as atopic dermatitis, psoriasis or urticaria. Other conditions characterized by elevated cytokine levels include cachexia, cachexia secondary to infection or malignancy, cachexia secondary to acquired immune deficiency syndrome (AIDS), ARC (AIDS related complex), fever and myalgias due to infection, cerebral malaria, osteoporosis and bone resorption diseases, keloid formation, scar tissue formation or pyrexia.

In particular, TNFα has been implicated in various roles with respect to human acquired immune deficiency syndrome (AIDS). AIDS results from the infection of T-lymphocytes with Human Immunodeficiency Virus (HIV), although HIV also infects and is maintained in myeloid lineage cells. TNF has been shown to upregulate HIV infection in T-lymphocytic and monocytic cells (see Poli, et al, Tumor necrosis factor alpha functions in an autocrine manner in the induction of human immunodeficiency virus expression, Proc Natl Acad Sci 87:782–785, 1990).

Several properties of TNFα such as stimulation of collagenases, stimulation of angiogenesis in vivo, stimulation of bone resorption and ability to increase the adherence of tumor cells to endothelium are consistent with a role for TNF in the development and metastatic spread of cancer in the host. TNFα has recently been directly implicated in the promotion of growth and metastasis of tumor cells (see Orosz, et al, Enhancement of experimental metastasis by tumor necrosis factor, J Exp Med 177:1391–1398, 1993).

Accordingly, chemical compounds which selectively inhibit PDE-IV would be useful in the treatment of allergic or inflammatory diseases or other diseases associated with excessive or unregulated production of cytokines, such as TNF. In addition, PDE-IV inhibitors would be useful for treatment of diseases which are associated with elevated cAMP levels or PDE-IV function in a particular target tissue. For example, PDE-IV inhibitors could be used in the treatment of diabetes insipidus (Kidney Int. 37:362, 1990; Kidney Int. 35:494, 1989) and central nervous system disorders, such as depression and multi-infarct dementia (see Eckman, et al, Curr. Ther. Res. 43:291, 1988; Nicholson, Psychopharmacology 101:147, 1990). Another application involving the use of PDE-IV inhibitors concerns modulating bronchodilatory activity via direct action on bronchial smooth muscle cells for the treatment of asthma.

SUMMARY OF THE INVENTION

The present invention comprises the genus of compounds represented by Formula (I):

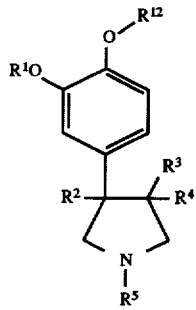

FORMULA I wherein $R^1$, $R^2$, $R^3$, $R^4$, $R^5$ and $R^{12}$ are defined hereinafter. Also part of the present invention are pharmaceutical compositions comprising one or more of the compounds of Formula (I) as well as their use, methods for their preparation and intermediates involved in the synthesis of the same.

DETAILED DESCRIPTION OF THE INVENTION

Figure 1:
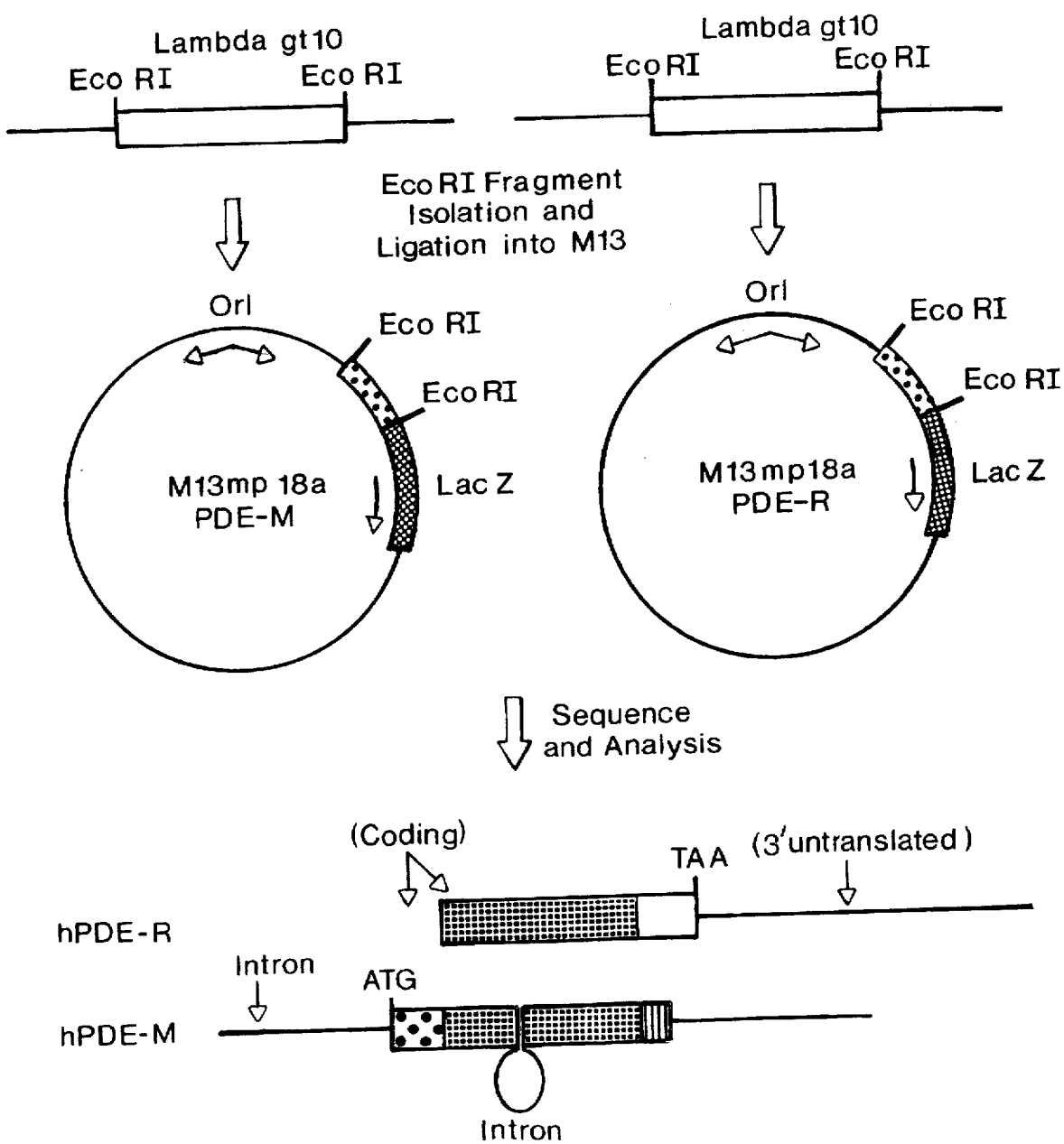
FIG. 1 sets forth the DNA sequence analysis of hPDE-M and hPDE-R.

The present invention comprises the genus of compounds represented by Formula (I):

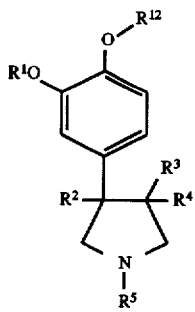

(I)

wherein $R^1$ is alkyl, haloalkyl, cycloalkyl, bridged polycycloalkyl, aryl, heteroaryl, aralkyl, heteroaralkyl or aryloxyalkyl;

$R^2$ is H, alkyl, haloalkyl, cycloalkyl, aryl, —CO-alkyl, —CO-cycloalkyl, —CO-aryl, —COO-alkyl, —COO-cycloalkyl, —COO-aryl, CH$_2$OH, CH$_2$—O-alkyl, —CHO, —CN, —NO$_2$ or SO$_2$R$^{10}$;

$R^3$ is —CO-alkyl, —CO-haloalkyl, —CO-cycloalkyl, —COO-alkyl, —COO-cycloalkyl, —COOH, —CO-aryl, —CONR$^6$R$^7$, —CH$_2$OH, —CH$_2$O-alkyl, —CHO, —CN, —NO$_2$, —NR$^8$COR$^9$, —NR$^8$SO$_2$R$^{10}$ or —SO$_2$R$^{10}$;

$R^4$ is H, alkyl, haloalkyl, cycloalkyl, —CO-alkyl, —CO-haloalkyl, —CO-cycloalkyl, —COO-alkyl, —COO-cycloalkyl, —COOH, —CO-aryl, —CONR$^6$R$^7$, —CN, —CHO or SO$_2$R$^{10}$;

$R^5$ is —CN or —C(X)—R$^{11}$ or SO$_2$R$^{10}$;

$R^6$ and $R^7$ are independently selected from H, alkyl, cycloalkyl, aryl or aralkyl or $R^6$ and $R^7$ together form a 4- to 7-membered heterocyclic or carbocyclic ring;

$R^8$ is H, alkyl or cycloalkyl;

$R^9$ is alkyl, cycloalkyl, aryl, alkoxy, aralkoxy or —NR$^6$R$^7$;

$R^{10}$ is alkyl, cycloalkyl, trifluoromethyl, aryl, aralkyl or —NR$^6$R$^7$;

$R^{11}$ is H, alkyl, haloalkyl, cycloalkyl, aryl, aralkyl, heteroaryl, C$_{1-6}$alkoxy, aralkoxy, aryloxy or —NR$^6$R$^7$;

$R^{12}$ is C$_{1-3}$alkyl, cyclopropyl or C$_{1-3}$haloalkyl; and

X is O or S.

As provided herein, the term "alkyl", alone or in combination, is defined herein to include straight chain or branched chain saturated hydrocarbon groups from C$_1$-C$_7$. The term "lower alkyl" is defined herein as C$_1$-C$_4$. Exemplary alkyl groups include methyl, ethyl, n-propyl, isopropyl, isobutyl, n-butyl, n-hexyl, and the like. The term "haloalkyl" is defined herein as a lower alkyl substituted with one or more halogens. The term "cycloalkyl" is defined herein to include cyclic hydrocarbon radicals from C$_3$-C$_7$. Exemplary cycloalkyl radicals include cyclopropyl, cyclobutyl, cyclobutyl, and cyclopentyl.

The term "alkoxy", alone or in combination, is defined herein to include an alkyl group, as defined earlier, which is attached through an oxygen atom to the parent molecular subunit. Exemplary alkoxy groups include methoxy, ethoxy, n-propoxy, isopropoxy, isobutoxy, n-butoxy, and the like.

The term "aryl", alone or in combination, is defined herein as a monocyclic or polycyclic group, preferably a monocyclic or bicyclic group, i.e. phenyl or naphthyl, which can be unsubstituted or substituted, for example, with one or more and, in particular, one to three substituents selected from halogen, alkyl, hydroxy, alkoxy, haloalkyl, nitro, amino, acylamino, alkylthio, alkylsulfinyl and alkylsulfonyl. Exemplary aryl groups include phenyl, 2-chlorophenyl, 3-chlorophenyl, 4-chlorophenyl, 2-methylphenyl, 4-methoxyphenyl, 3-trifluoromethylphenyl, 4-nitropohenyl, and the like.

The term "aralkyl" is defined herein as an alkyl group, as defined earlier, in which one of the hydrogen atoms is replaced by a phenyl group, an aryl or heteroaryl group as defined herein or a phenyl group carrying one or more substituents selected from, for example, halogen, alkyl, alkoxy and the like.

The term "aralkoxy", alone or in combination, is defined herein to include an aralkyl group, as defined earlier, which is attached through an oxygen atom to the parent molecular subunit. Exemplary aralkoxy groups include phenylmethoxy, phenylethoxy, phenylpropoxy and the like.

The term "heteroaryl" is defined herein as a 5-membered or 6-membered heterocyclic aromatic group which can optionally carry a fused benzene ring and which can be unsubstituted or substituted, for example, with one or more and, in particular, one to three substituents selected from halogen, alkyl, hydroxy, alkoxy, haloalkyl, nitro, amino, acylamino, alkylthio, alkylsulfinyl and alkylsulfonyl.

The term "halogen" is defined herein to include fluorine, chlorine, bromine and iodine.

The term "heteroaralkyl" is defined similarly as the term "aralkyl", however with the replacement of the aryl group with a heteroaryl group.

The term "bridged polycycloalkyl", as set forth herein, is intended to include bridged polycyclics of 6 to 12 carbons (e.g. bridged bicycloalkyls such as bicyclo[2.2.1]heptyl, bicyclo[2.2.2]octyl and bicyclo[3.2.1]octyl.)

Those skilled in the art will recognize that stereocenters exist in compounds of Formula (I). Accordingly, the present invention includes all possible stereoisomers and geometric isomers of Formula (I) and includes not only racemic compounds but also the optically active isomers as well. When a compound of Formula (I) is desired as a single enantiomer, it may be obtained either by resolution of the final product or by stereospecific synthesis from either isomerically pure starting material or any convenient intermediate. Resolution of the final product, an intermediate or a starting material may be effected by any suitable method known in the art. See, for example, *Stereochemistry of Carbon Compounds* by E. L. Eliel (Mcgraw Hill, 1962) and *Tables of Resolving Agents* by S. H. Wilen. Additionally, in situations where tautomers of the compounds of Formula (I) are possible, the present invention is intended to include all tautomeric forms of the compounds.

Some specific compounds of Formula (I) are listed below, the synthesis of which was performed in accordance with the Example section set forth below.

1. cis-3-(3-cyclopentoxy-4-methoxyphenyl)-1-(1,1-dimethylethoxycarbonyl)-4-(methoxycarbonyl)pyrrolidine;
2. trans-3-(3-cyclopentoxy-4-methoxyphenyl)-1-(1,1-dimethylethoxycarbonyl)-4-(methoxycarbonyl)pyrrolidine;
3. trans-3-methoxycarbonyl-1-(1,1-dimethylethoxycarbonyl)-4-[3-(3-phenoxypropoxy)-4-methoxyphenyl]pyrrolidine;
4. trans-3-(3,4-dimethoxyphenyl)-1-(1,1-dimethylethoxycarbonyl)-4-(methoxycarbonyl)pyrrolidine;
5. 3-(3-cyclopentoxy-4-methoxyphenyl)-1-(1,1-dimethylethoxycarbonyl)-3-(methoxycarbonyl)pyrrolidine;
6. trans-3-(3-cyclopentoxy-4-methoxyphenyl)-1-(1,1-dimethylethoxycarbonyl)-4-(hydroxymethyl)pyrrolidine;
7. trans-3-(3-cyclopentoxy-4-methoxyphenyl)-4-hydroxymethyl-1-(methoxycarbonyl)pyrrolidine;
8. trans-1-aminocarbonyl-3-(3-cyclopentoxy-4-methoxyphenyl)-4-(methoxycarbonyl)pyrrolidine;
9. cis-1-aminocarbonyl-3-(3-cyclopentoxy-4-methoxyphenyl)-4-(methoxycarbonyl)pyrrolidine;
10. 1-aminocarbonyl-3-(3-cyclopentoxy-4-methoxyphenyl)-3-(methoxycarbonyl)pyrrolidine;
11. trans-1-methoxycarbonyl-3-methoxycarbonyl-4-(3-phenylmethoxy-4-methoxyphenyl)pyrrolidine;
12. 3-(3-cyclopentoxy-4-methoxyphenyl)-1-methoxycarbonyl-4-methyl-4-(methylcarbonyl)pyrrolidine;
13. trans-3-(3-cyclopentoxy-4-methoxyphenyl)-4-(1,1-dimethylethoxycarbonyl)-1-(methoxycarbonyl)pyrrolidine;
14. 3-(3-cyclopentoxy-4-methoxyphenyl)-4-(1,1-dimethylethoxycarbonyl)-1-methoxycarbonyl-4-methylpyrrolidine;
15. trans-3-(3-cyclopentoxy-4-methoxyphenyl)-4-ethylcarbonyl-1-(methoxycarbonyl)pyrrolidine;
16. trans-1-methoxycarbonyl-3-nitro-4-[3-(3-phenoxypropoxy)-4-methoxyphenyl]pyrrolidine;
17. trans-3-cyano-4-(3-cyclopentoxy-4-methoxyphenyl)-1-(methoxycarbonyl)pyrrolidine;
18. trans-3-(3-cyclopentoxy-4-methoxyphenyl)-1-methoxycarbonyl-4-nitropyrrolidine;
19. trans-3-(3-cyclopentoxy-4-methoxyphenyl)-1-methoxycarbonyl-4-(methylcarbonyl)pyrrolidine;
20. trans-3-(3-cyclopentoxy-4-methoxyphenyl)-1-methoxycarbonyl-4-(phenylcarbonyl)pyrrolidine;
21. trans-1-methoxycarbonyl-3-methoxycarbonyl-4-[3-(3-phenoxypropoxy)-4-methoxyphenyl]pyrrolidine;
22. 3-(3-cyclopentoxy-4-methoxyphenyl)-4-ethoxycarbonyl-1-methoxycarbonyl-4-methylpyrrolidine;
23. 3-(3-cyclopentoxy-4-methoxyphenyl)-4-methoxycarbonyl-1-methoxycarbonyl-4-methylpyrrolidine;
24. trans-3-(3-cyclopentoxy-4-methoxyphenyl)-1-methoxycarbonyl-4-(methylcarbonyl)pyrrolidine;
25. trans-3-(3-cyclopentoxy-4-methoxyphenyl)-4-methoxycarbonyl-1-(methylcarbonyl)pyrrolidine;
26. trans-3-(3-cyclopentoxy-4-methoxyphenyl)-1-ethylcarbonyl-4-(methoxycarbonyl)pyrrolidine;
27. trans-3-(3-cyclopentoxy-4-methoxyphenyl)-1-(1-imidazolylcarbonyl)-4-(methoxycarbonyl)pyrrolidine;
28. trans-3-(3-cyclopentoxy-4-methoxyphenyl)-1-formyl-4-(methoxycarbonyl)pyrrolidine;
29. trans-1-formyl-3-methoxycarbonyl-4-[3-(3-phenoxypropoxy)-4-methoxyphenyl]pyrrolidine;
30. trans-3-(3-cyclopentoxy-4-methoxyphenyl)-1-methoxycarbonyl-4-(1-methylethoxycarbonyl)pyrrolidine;
31. trans-3-(3-cyclopentoxy-4-methoxyphenyl)-4-ethoxycarbonyl-1-(methoxycarbonyl)pyrrolidine;
32. trans-3-carboxy-4-(3-cyclopentoxy-4-methoxyphenyl)-1-(1,1-dimethylethoxycarbonyl)pyrrolidine;
33. trans-3-carboxy-4-(3-cyclopentoxy-4-methoxyphenyl)-1-(methoxycarbonyl)pyrrolidine;
34. trans-3-carboxy-4-(3-cyclopentoxy-4-methoxyphenyl)-1-(phenylmethoxycarbonyl)pyrrolidine;
35. trans-3-carboxy-4-(3-cyclopentoxy-4-methoxyphenyl)-1-(1-methylethoxycarbonyl)pyrrolidine;
36. trans-3-carboxy-1-(methoxycarbonyl)-4-[3-(3-phenoxypropoxy)-4-methoxyphenyl]pyrrolidine;
37. trans-3-carboxy-4-(3-cyclopentoxy-4-methoxyphenyl)-1-formylpyrrolidine;
38. trans-1-aminocarbonyl-3-carboxy-4-(3-cyclopentoxy-4-methoxyphenyl)pyrrolidine;
39. trans-3-aminocarbonyl-4-(3-cyclopentoxy-4-methoxyphenyl)-1-(methoxycarbonyl)pyrrolidine;
40. trans-3-aminocarbonyl-4-(3-cyclopentoxy-4-methoxyphenyl)-1-(1,1-dimethylethoxycarbonyl)pyrrolidine;
41. trans-3-(3-cyclopentoxy-4-methoxyphenyl)-1-(1,1-dimethylethoxycarbonyl)-4-[(N-phenylmethyl)aminocarbonyl]pyrrolidine;
42. trans-3-(3-cyclopentoxy-4-methoxyphenyl)-4-N-(1,1-dimethylethoxycarbonyl)-1-(1,1-dimethylethoxycarbonyl)pyrrolidine;
43. trans-3-(3-cyclopentoxy-4-methoxyphenyl)-4-N-(1,1-dimethylethoxycarbonyl)-1-(methoxycarbonyl)pyrrolidine;
44. trans-3-(3-cyclopentoxy-4-methoxyphenyl)-4-N-(1,1-dimethylethoxycarbonyl)-1-(phenylmethoxycarbonyl)pyrrolidine;
45. trans-3-(3-cyclopentoxy-4-methoxyphenyl)-4-[N-(1,1-dimethylethoxycarbonyl)-N-methyl]-1-(phenylmethoxycarbonyl)pyrrolidine;
46. trans-3-(3-cyclopentoxy-4-methoxyphenyl)-4-N-(methylsulfonyl)-1-(phenylmethoxycarbonyl)pyrrolidine;
47. trans-3-(3-cyclopentoxy-4-methoxyphenyl)-1-(phenylmethoxycarbonyl)-4-N-(trifluoromethylsulfonyl)pyrrolidine;

48. trans-3-(3-cyclopentoxy-4-methoxyphenyl)-4-N-(phenylsulfonyl)-1-(phenylmethoxycarbonyl)pyrrolidine;
49. trans-3-(3-cyclopentoxy-4-methoxy)phenyl)-1-methoxycarbonyl-4-N-(methoxycarbonyl)pyrrolidine;
50. trans-1-aminocarbonyl-3-(3-cyclopentoxy-4-methoxyphenyl)-4-N-(1,1-dimethylethoxycarbonyl)pyrrolidine;
51. trans-1-aminothiocarbonyl-3-(3-cyclopentoxy-4-methoxyphenyl)-4-(methoxycarbonyl)pyrrolidine;
52. trans-1-cyano-3-(3-cyclopentoxy-4-methoxyphenyl)-4-(methoxycarbonyl)pyrrolidine;
53. trans-3-(3-cyclopentoxy-4-methoxyphenyl)-4-methoxycarbonyl-1-(phenylmethoxycarbonyl)pyrrolidine;
54. trans-3-(3-cyclopentoxy-4-methoxyphenyl)-4-methoxycarbonyl-1-(methylethoxycarbonyl)pyrrolidine;
55. 3-(3-cyclopentoxy-4-methoxyphenyl)-1-(1,1-dimethylethoxycarbonyl)-4-methoxycarbonyl-4-methylpyrrolidine;
56. trans-3-(3-cyclopentoxy-4-methoxyphenyl)-1-methoxycarbonyl-4-(methoxymethyl)pyrrolidine.

Generally, compounds of Formula (I) can be prepared according to the following synthesis schemes. In all of the schemes described below, it is well understood in the art that protecting groups are employed where necessary in accordance with general principles of chemistry. These protecting groups are removed in the final steps of the synthesis under basic, acidic, or hydrogenolytic conditions which will be readily apparent to those skilled in the art. By employing appropriate manipulation and protection of any chemical functionalities, synthesis of any compounds of the Formula (I) not specifically set forth herein can be accomplished by methods analogous to the schemes set forth below as well as those described in the Example section.

One method for the preparation of compounds having Formula (I) uses an azomethine ylide cycloaddition reaction for the synthesis of the pyrrolidine ring. N-benzyl-N-methoxymethyl-N-trimethylsilylmethylamine, prepared by the procedure described by Padwa and coworkers (*J. Org. Chem.* 1987, 52, 235), is reacted with an appropriately substituted olefin according to the procedure of Achiwa and coworkers (*Chem. Pharm. Bull.* 1985, 33, 2762).

Such a cycloaddition reaction proceeds with aryl-substituted olefins bearing an electron-withdrawing group. The olefin can be prepared by any of a number of methods available including Horner-Emmons and Wittig chemistry. The preferred process for the cycloaddition reaction is in an inert solvent (e.g. methylene chloride, dioxane, tetrahydrofuran, toluene) under the influence of a suitable acid, such as trifluoroacetic acid, at temperatures ranging from -20°-30° C. Alternatively, one can affect the cycloaddition under the influence of lithium fluoride and sonication (Padwa, vide supra). For example, one particular approach for the cycloaddition reaction is shown below.

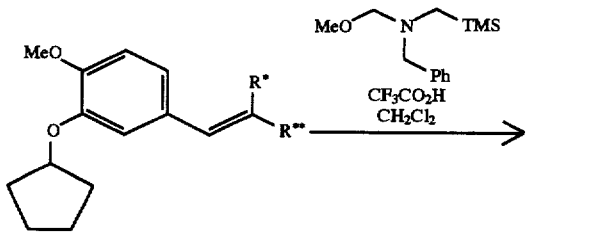

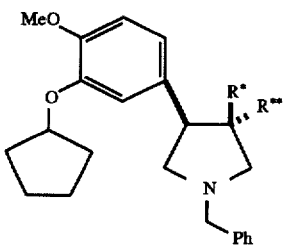

| R* | R** | Yield (%) |
|---|---|---|
| CO₂CH₃ | H | 77 |
| H | CO₂CH₃ | 86 |
| H | NO₂ | 56 |
| CH₃ | CO₂CH₂CH₃ | 87 |

(R* and R** are intended only to designate examples of functional groups that can be used to facilitate the cycloaddition reaction. One skilled in the art of organic synthesis will appreciate that other functional groups at R* and R** are acceptable and that appropriate manipulation of R* and R** may be required to complete the synthesis of compounds of Formula (I).)

The pyrrolidines obtained from the azomethine ylide cycloaddition can be converted into compounds of Formula (I) by methods available to one who is skilled in the art of organic synthesis. Reductive debenzylation of the pyrrolidine can be carried out by transfer hydrogenation (4% HCO₂H/MeOH;10% Pd/C) at room temperature. Other suitable methods for debenzylation (10% Pd/C, 50 psi H₂, acetic acid) can also be used. The free pyrrolidine can then be acylated under the influence of a suitable base and acylating reagent. Alternatively, debenzylation/N-acylation can be affected in one operation by reacting the 1-(phenylmethyl)pyrrolidine with a chloroformate in a suitable solvent (e.g., dichloroethane, acetonitrile, etc.) at temperatures between 30°–100° C. Some specific examples of these methods are shown below.

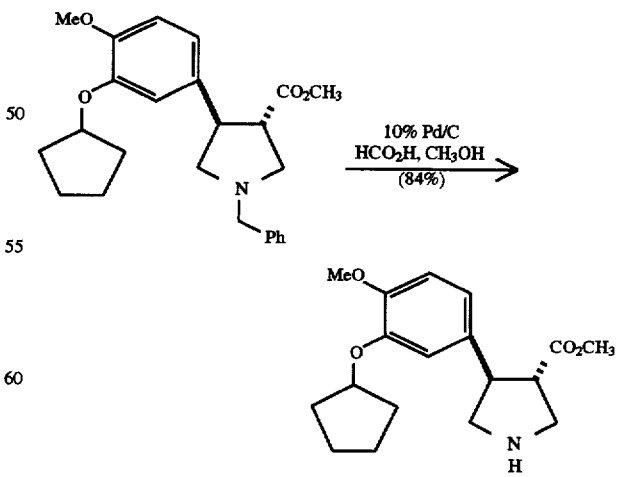

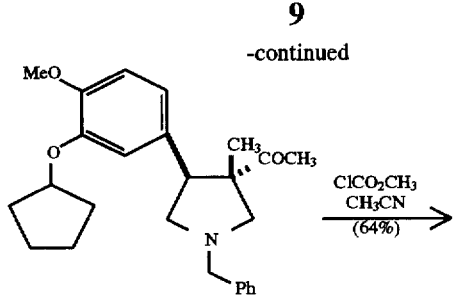

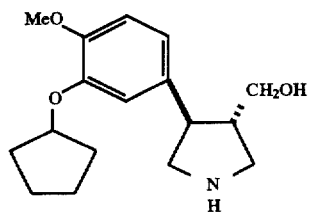

Compounds of Formula (I) in which $R^3$ is COOH may be obtained by saponification of the corresponding alkyl ester. The preferred method for saponification uses an alkali metal hydroxide (e.g., LiOH) at 0°–23° C. in an aqueous ethereal solvent system (e.g., 1:1, 1,4-dioxane:$H_2O$). A specific example of this chemistry is shown below.

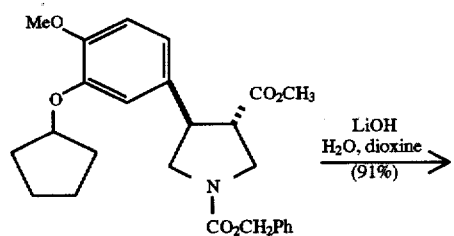

Compounds of Formula (I) in which $R^3$ is $CH_2OH$ can be obtained by a hydride reduction (e.g. LiAlH$_4$) of a 3-alkoxycarbonyl-4-aryl-1-(phenylmethyl)pyrrolidine or a 3-alkoxycarbonyl-4-arylpyrrolidine in an ethereal solvent (e.g., THF) at temperatures ranging from –10°–30° C. The 3-aryl-4-(hydroxymethyl)pyrrolidines can be selectively N-acylated according to standard procedures known to those skilled in the art of organic synthesis (e.g., Schotten-Baumann conditions). Specific examples of this chemistry are shown below.

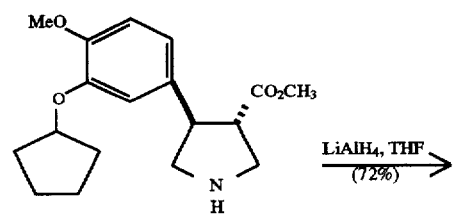

Compounds of Formula (I) in which $R^3$ is $CONR^6R^7$ can be obtained from the corresponding carboxylic acid. Treatment of the carboxylic acid with an activating reagent, such as 1,1'-carbonyldiimidazole (CDI), in a chlorinated solvent (e.g., $CH_2Cl_2$) followed by addition of an amine afforded, after purification of the amides. Specific examples of this chemistry are shown below.

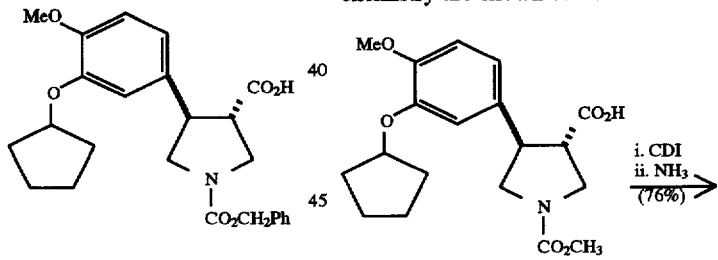

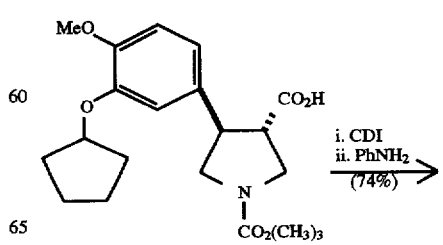

-continued

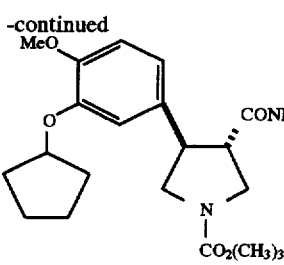

Compounds of Formula (I) where R⁵ is CN are prepared by one of two methods. The free pyrrolidine can be N-cyanated by treatment with cyanogen bromide (BrCN) in a suitable solvent (e.g., acetonitrile) in the presence of a base. Alternatively, the N-phenylmethylpyrrolidine obtained directly from the azomethine ylide cycloaddition can be treated with cyanogen bromide to affect an N-dealkylative cyanation reaction (von Braun reaction). These two methods are illustrated below.

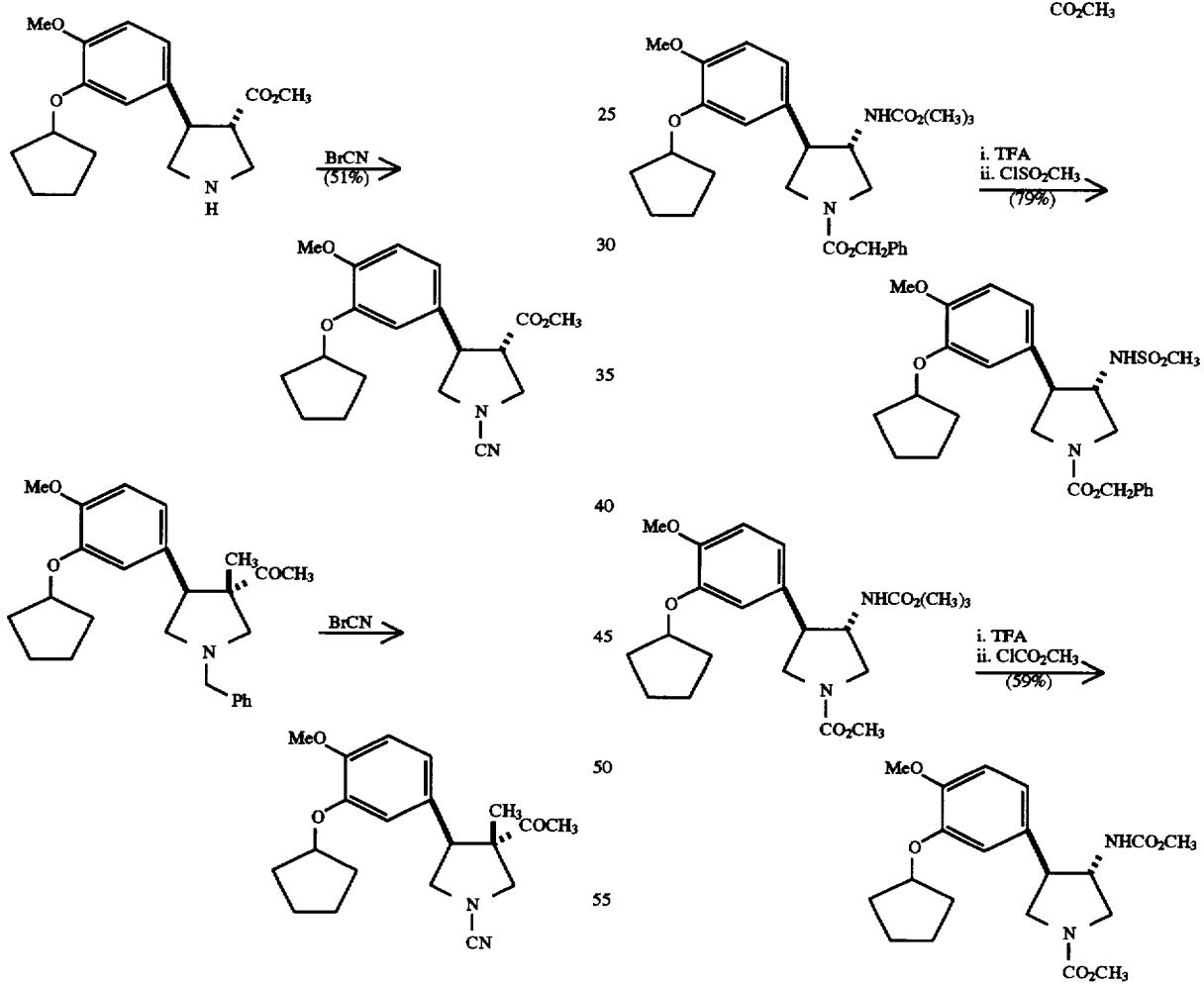

3-Amino-1-acylpyrrolidine derivatives (Formula (I) wherein $R^3/R^4$ is $NR^8COR^9/NR^8SO_2R^{10}$) were synthesized from the carboxylic acids by use of a Curtius rearrangement. Preferred conditions use diphenylphosphoryl azide (DPPA) in t-butanol at elevated temperature. The resulting t-butyl carbamate provides entry into the compounds of Formula (I). Solvolytic removal of the t-butyl carbamate under acidic conditions [e.g., trifluoroacetic acid (TFA)], followed by acylation of the resulting primary amine affords the compound of Formula (I). Specific examples of this chemistry are shown below.

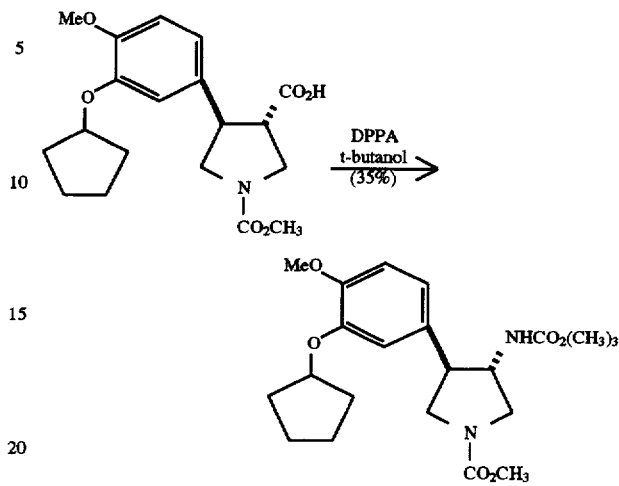

GENERAL PROCEDURES

Unless otherwise noted all starting materials were obtained from commercial suppliers and used without further purification. All reactions involving oxygen- or moisture-sensitive compounds were performed under a dry $N_2$ atmosphere. All reactions and chromatography fractions were analyzed by thin-layer chromatography on 250-mm silica gel plates, visualized with UV light and I₂ stain. Flash column chromatography was carried out using Merck silica gel 60 (230–400 mesh).

¹H-NMR spectra were measured in CDCl₃ using either a Varian VXZ-300 or a Varian Unity-300 instrument. J values are reported in Hertz. Chemical shifts are expressed in ppm downfield from internal tetramethylsilane. Apparent multiplicities are designated as s, singlet; d, doublet; t, triplet; q, quartet; m, multiplat; b, broad. All mass spectra were taken in the positive ion mode under electrospray ionization (ESI), chemical ionization (CI), electron impact (EI), or by fast-atom bombardment (FAB). Melting points were determined on a Thomas-Hoover Capillary Melting Point Apparatus and are uncorrected. Elemental analyses were performed by Atlantic Microlab, Norcross, Ga.

The following section describes the preparation of intermediates that may be used in the synthesis of compounds of Formula (I).

(A). (E)-Methyl-3-(3-cyclopentoxy-4-methoxyphenyl)-prop-2-en-oate

To a solution of trimethylphosphonoacetate (13 mL, 82 mmol) in 36 mL of THF at 0° C. was added lithium bis(trimethylsilyl)amide (82 mL of 1M THF solution, 82 mmol). This solution was stirred for 20 min, and a solution of 3-cyclopentoxy-4-methoxybenzaldehyde (15 g, 68 mmol) in 30 mL of THF was then added dropwise via addition funnel. When reaction was judged complete by TLC analysis, the reaction was diluted with ethyl acetate:hexanes (1:1), and the organic layer was washed with H₂O and brine. The organic layer was dried over MgSO₄, filtered, and concentrated under reduced pressure to afford (E)-methyl-3-(3-cyclopentoxy-4-methoxyphenyl)-prop-2-en-oate as a pale yellow solid (17.2 g, 92%). ¹H-NMR (300 MHz): δ 3.79 (s, 3), 3.86 (s, 3), 6.28 (d, 1, J=16), 7.52 (d, 1, J=16).

The following compounds were prepared according to the general procedure set forth above.

(B). (E)-methyl-3-[3-(3-phenoxypropoxy)-4-methoxyphenyl]-prop-2-en-oate:

100%; ¹H-NMR (300 MHz): δ 2.33 (q, 2, J=6.1), 3.79 (s, 3), 3.87 (s, 3), 4.19 (t, 2, J=6.1), 4.25 (t, 2, J=6.1), 6.29 (d, 1, J=16), 7.61 (d, 1, J=16).

(C). (E)-1,1-Dimethylethyl-3-(3-cyclopentoxy-4-methoxyphenyl)-prop-2-en-oate

To a solution of t-butyl diethylphosphonoacetate (5.0 g, 19.8 mmol) in 15 mL of THF at 0° C. was added lithium bis(trimethylsilyl)amide (19.8 mL of 1M THF solution, 19.8 mmol). This solution was stirred for 20 min, and a solution of 3-cyclopentoxy-4-methoxybenzaldehyde (3.64 g, 16.5 mmol) in 15 mL of THF was then added dropwise via addition funnel. After 1 hr the reaction was judged complete by TLC analysis and was diluted with ether. The organic layer was washed with H₂O and brine, dried over MgSO₄, filtered, and concentrated under reduced pressure to an oil. Silica gel chromatography (6:1:1, hexanes:ethyl acetate:CH₂Cl₂) provided an oil which was further chromatographed (8:1:1, hexanes:ethyl acetate:CH₂Cl₂) to afford (E)-1,1-dimethylethyl-3-(3-cyclopentoxy-4-methoxyphenyl)-prop-2-en-oate (5.0 g, 95%) as a pale yellow oil. ¹H-NMR (300 MHz): δ 1.52 (s, 9), 3.86 (s, 3). Anal. Calcd for C₁₉H₂₆O₄: C, 71.67; H, 8.23. Found: C, 71.70; H, 8.25.

(D). (E)-1,1-Dimethylethyl-3-(3-cyclopentoxy-4-methoxyphenyl)-2-methyl-prop-2-en-oate To a solution of t-butyl diethylphosphonoacetate (5.0 g, 19.8 mmol) in 40 mL of THF at −23° C. (ice:acetone) was added lithium bis(trimethylsilyl)amide (19.8 mL of 1M THF solution, 19.8 mmol). This solution was stirred for 15 min, and CH₃I (2.8 g, 21.8 mmol). After 24 hr the reaction was diluted with ether and washed successively with 1M H₃PO₄, H₂O, and brine. The solution was dried (MgSO₄), filtered and concentrated under reduced pressure to an oil (5.4 g). ¹H-NMR analysis indicated an approximate 1:1 mixture of starting phosphonoacetate and the monomethylated derivative, which was taken on without further purification.

The phosphonoacetate mixture described above was dissolved in THF (20 mL) and cooled to 0° C. To this solution was added lithium bis(trimethylsilyl)amide (19.8 mL of 1M THF solution, 19.8 mmol). After 15 min., a solution of 3-cyclopentoxy-4-methoxybenzaldehyde (3.64 g, 16.5 mmol) in THF (20 mL) was then added dropwise via addition funnel. When the reaction was judged complete by TLC analysis, the reaction mixture was diluted with ether. The organic layer was washed with H₂O and brine, dried over MgSO₄, filtered and concentrated under reduced pressure to an oil (6.5 g). Silica gel chromatography (10:1, hexanes:ethyl acetate) provided (E)-1,1-dimethylethyl-3-(3-cyclopentoxy-4-methoxyphenyl)-2-methyl-prop-2-en-oate as an oil (797 mg, 12%). The remaining chromatography fractions contained product mixtures. Anal. Calcd for C₂₀H₂₈O₄: C, 72.26; H, 8.49 Found: C, 72.31; H, 8.56.

(E). (E)-Ethyl-3-(3-cyclopentoxy-4-methoxyphenyl)-2-methyl-prop-2-en-oate

To a solution of triethyl 2-methylphosphonopropionate (3.6 g, 15 mmol) in 30 mL of THF at 0° C. was added lithium bis(trimethylsilyl)amide (18 mL of 1M THF solution, 18 mmol). This solution was stirred for 30 min, and a solution of 3-cyclopentoxy-4-methoxybenzaldehyde (2.75 g, 12.5 mmol) in 5 mL of THF was then added dropwise. After 4 hr the reaction was judged complete by TLC analysis and was diluted with ethyl acetate:hexanes (1:1). The organic layer was washed with H₂O and brine, dried over MgSO₄, filtered, and concentrated under reduced pressure. Silica gel chromatography (4:1, hexanes:ethyl acetate) provided (E)-ethyl-3-(3-cyclopentoxy-4-methoxyphenyl)-2-methyl-prop-2-en-oate (2.75 g, 72%) as a colorless oil that solidified on standing. ¹H-NMR (300 MHz): δ 1.35 (t, 3, J=7.1), 2.14 (s, 3), 3.88 (s, 3), 4.27 (q, 2, J=7.3), 7.62 (s, 1). Anal. Calcd for C₁₈H₂₄O₄: C, 71.03; H, 7.95. Found: C, 70.88; H, 7.99.

(F). (E)-Methyl-3-(3-cyclopentoxy-4-methoxyphenyl)-2-methyl-prop-2-en-oate

To a solution of (E)-ethyl-3-(3-cyclopentoxy-4-methoxyphenyl)-2-methyl-prop-2-en-oate (970 mg, 3.2 mmol) in 3 mL of 1,4-dioxane was added a solution of LiOH•H₂O (156 mg, 3.8 mmol) in 3 mL of H₂O. The resulting mixture was heated at 80° C. for 2 hr and 45° C. for 16 hr. The resulting solution was diluted with ether and poured into 1M H₃PO₄. The aqueous layer was extracted with ethyl acetate (2×), washed with brine, dried (MgSO₄), filtered, and concentrated under reduced pressure. Silica gel chromatography (95:5, CH₂Cl:methanol) provided (E)-3-(3-cyclopentoxy-4-methoxyphenyl)-2-methyl-prop-2-enoic acid as a colorless solid (700 mg, 79%). Anal. Calcd for C₁₆H₂₀O₄: C, 69.55; H, 7.29. Found: C, 69.39; H, 7.29.

The carboxylic acid thus obtained (610 mg, 2.2 mmol) was dissolved in 10 mL of methanol and 3 drops of con. H₂SO₄ was added. The resulting solution was heated to reflux for 20 hr, cooled to room temperature, and partitioned between sat. NaHCO₃ and CH₂Cl₂. The aqueous layer was extracted with CH₂Cl₂ (2×) and the combined organic layers were dried (MgSO₄), filtered, and concentrated under reduced pressure to an oil. Silica gel chromatography (4:1, hexanes:ethyl acetate) afforded (E)-methyl-3-(3-cyclopentoxy-4-methoxyphenyl)-2-methyl-prop-2-en-oate as a colorless solid (610 mg, 96%). ¹H-NMR (300 MHz): d 2.15 (d, 3, J=1.2), 3.81 (s, 3), 3.88 (s, 3), 7.63 (s, 1). Anal. Calcd for $C_{17}H_{22}O_4$: C, 70.32; H, 7.64. Found: C, 70.44; H, 7.72.

(G). (E)-4-(3-Cyclopentoxy-4-methoxyphenyl)-3-methyl-but-3-en-2-one

To a solution of (E)-3-(3-cyclopentoxy-4-methoxyphenyl)-2-methyl-prop-2-enoic acid (2.21 g, 8.0 mmol) in $CH_2Cl_2$ (16 mL) was added 1,1'-carbonyldiimidazole (8.8 mmol, 1.43 g). The resulting solution was stirred for 10 min and $NH(CH_3)OCH_3 \cdot HCl$ (12 mmol, 1.16 g) was added. The mixture was stirred at rt for 16 hr, and triethylamine (800 mg) was added. This was stirred an additional 30 min. The solution was diluted with $CH_2Cl_2$ and washed successively with 1M $H_3PO_4$ and $H_2O$. The organic layers were dried ($K_2CO_3$), filtered and evaporated to a yellow oil. Silica gel chromatography (6:4:1, hexanes:ethyl acetate:$CH_2Cl_2$) provided the N-methyl-N-methoxyamide as a pale yellow oil (2.1 g, 82%). Anal. Calcd for $C_{18}H_{25}NO_4$: C, 67.69; H, 7.89; N, 4.39. Found: C, 67.48; H, 7.95; N, 4.35.

The amide thus obtained (1.01 g, 3.17 mmol) was dissolved in THF (6 mL), cooled to 0° C. and treated dropwise with $CH_3Li$ (4.0 mL of a 1.4M ether solution). The yellow solution was stirred for 15 min, diluted with ether and washed successively with 1M H3PO4 and brine. The solution was dried (MgSO4), filtered and concentrated under reduced pressure to afford (E)-4-(3-cyclopentoxy-4-methoxyphenyl)-3-methyl-but-3-en-2-one as a yellow oil (832 mg, 96%). $^1$H-NMR (300 MHz): δ 2.09 (d, 3, J=1.2), 2.46 (s, 3), 3.89 (s, 3), 7.47 (s, 1).

(H). (Z)-Methyl-3-(3-cyclopentoxy-4-methoxyphenyl)-prop-2-enoate

To a solution of 18-crown-6 (17 g, 64 mmol) and bis(2,2,2-trifluoroethyl)(methoxycarbonylmethyl)phosphonate (4.5 g, 14 mmol) in 200 mL of THF was added potassium bis(trimethylsilyl)amide (31 mL of 0.5M THF solution, 15.5 mmol). After 15 min a solution of 3-cyclopentoxy-4-methoxybenzaldehyde (2.8 g, 13 mmol) in 5 mL of THF was then added dropwise. The resulting solution was stirred at −78° C. for 30 min and quenched with sat $NH_4Cl$. The mixture was diluted with ether and washed with 1M $H_3PO_4$, $H_2O$, and brine. The organic layer was dried over $MgSO_4$, filtered, and concentrated under reduced pressure. Silica gel chromatography (3:1, hexanes:ethyl acetate) provided (Z)-methyl-3-(3-cyclopentoxy-4-methoxyphenyl)-prop-2-enoate (3.1 g, 87%), containing a trace amount of the E-isomer. $^1$H-NMR (300 MHz): δ 3.74 (s, 3), 3.89 (s, 3), 5.82 (d, 1, J=13).

(I). (E)-3-Cyclopentoxy-4-methoxycinnamonitrile

To a slurry of NaH (1.1 g, 27.5 mmol) in 80 mL of THF at 0° C. was added dropwise a solution of diethyl cyanomethylphosphonate (4.42 g, 24.9 mmol) in 20 mL of THF. The mixture was stirred for 30 min, and a solution of 3-cyclopentoxy-4-methoxybenzaldehyde (5.0 g, 22.7 mmol) in 20 mL of THF was then added dropwise. The mixture was stirred for 2 hr and then diluted with ether. The mixture was washed with 1M $H_3PO_4$, $H_2O$, and brine. The organic layer was dried over $MgSO_4$, filtered, and concentrated under reduced pressure to yield 3-cyclopentoxy-4-methoxycinnamonitrile (4.8 g, 87%) as a yellow oil, which was carried on without further purification. $^1$H-NMR (300 MHz): δ 3.89 (s, 3), 5.69 (d, 1, J=16.6).

(J). (E)-N-Methyl-N-methoxy-3-(3-cyclopentoxy-4-methoxyphenyl)-prop-2-enamide

To a solution of 3-cyclopentoxy-4-methoxybenzaldehyde (2.2 g, 10 mmol) in 15 mL of $CH_2Cl_2$ was added N-methoxy-N-methyl-2-(triphenylphospohoranylidene) acetamide (7.2 g, 20 mmol). The resulting solution was stirred for 12 hr at room temperature. Concentration under reduced pressure followed by silica gel chromatography (6:4:1, hexanes:ethyl acetate:$CH_2Cl_2$) provided (E)-N-methyl-N-methoxy-3-(3-cyclopentoxy-4-methoxyphenyl)-prop-2-enamide as a pale yellow oil (2.6 g, 87%). $^1$H-NMR (300 MHz): δ 3.31 (s, 3), 3.77 (s, 3), 3.88 (s, 3).

(K). (E)-4-(3-Cyclopentoxy-4-methoxyphenyl)-but-3-en-2-one

To a solution of (E)-N-methoxy-N-methyl-3-(3-cyclopentoxy-4-methoxyphenyl)-prop-2-enamide (318 mg, 1.05 mmol) in 2.5 mL of THF cooled to 0° C. was added $CH_3Li$ (1.5 mL of 1.4M ether solution). The resulting solution was stirred for 5 min, diluted with ether and transferred to a separatory funnel. After washing with $H_2O$, 1M $H_3PO_4$, and brine, the organic layer was dried over $MgSO_4$, filtered, and concentrated under reduced pressure. Silica gel chromatography (3:1, hexanes:ethyl acetate) provided (E)-4-(3-cyclopentoxy-4-methoxyphenyl)-but-3-en-2-one as a white solid (234 mg, 90%). $^1$H-NMR (300 MHz): δ 2.38 (s, 3), 3.89 (s, 3), 6.59 (d, 1, J=16), 7.46 (d, 1, J=16).

(L). (E)-5-(3-Cyclopentoxy-4-methoxyphenyl)-pent-4-en-3-one

To a solution of (E)-N-methoxy-N-methyl-3-(3-cyclopentoxy-4-methoxyphenyl)-prop-2-enamide (1.33 g, 4.36 mmol) in 8.0 mL of THF cooled to 0° C. was added $CH_3CH_2MgBr$ (9 mL of 1.0M THF solution). The resulting solution was stirred for 30 min, diluted with ether and transferred to a separatory funnel. After washing with $H_2O$, 1M $H_3PO_4$, and brine, the organic layer was dried over $MgSO_4$, filtered, and concentrated under reduced pressure. Silica gel chromatography (4:1, hexanes:ethyl acetate) provided (E)-5-(3-cyclopentoxy-4-methoxyphenyl)-pent-4-en-3-one as a white solid (400 mg, 34%). $^1$H-NMR (300 MHz): δ 1.17 (t, 3, J=7.6), 2.69 (q, 2, J=7.3), 3.89 (s, 3), 6.59 (d, 1, J=16), 7.50 (d, 1, J=16). Anal. Calcd for $C_{17}H_{22}O_3$: C, 74.42; H, 8.08. Found: C, 74.52; H, 8.13.

(M). (E)-3-(3-Cyclopentoxy-4-methoxyphenyl)-1-phenylprop-2-enone

To a solution of (E)-N-methoxy-N-methyl-3-(3-cyclopentoxy-4-methoxyphenyl)-prop-2-enamide (1.25 g, 4.0 mmol) in 10 mL of THF cooled to 0° C. was added PhLi (2.5 mL of 1.8M ether/cyclohexane solution). The resulting solution was stirred at 0° C. for 1 hr, at which time an additional 0.5 mL of PhLi was added. After 10 min the solution was diluted with ether and treated with 5 mL of 1N HCl. After washing with $H_2O$ and brine, the organic layer was dried over $MgSO_4$, filtered, and concentrated under reduced pressure. Silica gel chromatography (3:1, hexanes:ethyl acetate) provided (E)-3-(3-cyclopentoxy-4-methoxyphenyl)-1-phenylprop-2-enone as a yellow oil (808 mg, 62%).

(N). trans-3-(3-Cyclopentoxy-4-methoxyphenyl)-4-methoxycarbonyl-1-(phenylmethyl)pyrrolidine To a solution of N-methoxymethyl-N-(phenylmethyl) trimethylsilylmethylamine (2.84 g, 12 mmol) and (E)-methyl 3-(3-cyclopentoxy-4-methoxyphenyl)prop-2-enoate (2.76 g, 10 mmol) in 20 mL of $CH_2Cl_2$ cooled to 0° C. was added a 1 mL of a 1M solution of trifluoroacetic acid. Stirring was continued for 12 hr, and the solution was partitioned between ether and sat. $NaHCO_3$. The layers were separated and the aqueous layer was extracted ethyl acetate (2×). The combined organic layers were dried ($K_2CO_3$), filtered, and concentrated under reduced pressure to a pale yellow oil. Chromatography on silica gel (3:1, hexanes:ethyl acetate) provided trans-3-(3-cyclopentoxy-4-methoxyphenyl)-4-methoxycarbonyl-1-(phenylmethyl)

pyrrolidine (3.5 g, 86%) as a colorless oil. $^1$H-NMR (300 MHz): δ 2.74–3.09 (m, 5), 3.67 (s, 3), 3.81 (s, 3), 4.75 (m, 1).

The following compounds were prepared according to the general procedure as set forth above.

(O). cis-3-(3-cyclopentoxy-4-methoxyphenyl)-4-methoxycarbonyl-1-(phenylmethyl)pyrrolidine:

77%; $^1$H-NMR (300 MHz): δ 3.2 (s, 3), 3.75 (s, 2), 3.8 (s, 3).

(P). trans-3-methoxycarbonyl-4-[3-(3-phenoxypropoxy)-4-methoxyphenyl]-1-(phenylmethyl)pyrrolidine:

98%; Anal. Calcd for $C_{29}H_{33}NO_5$: C, 73.24; H, 6.99; N, 2.95. Found: C, 73.17; H, 7.02; N, 2.99.

(Q). trans-3-methoxycarbonyl-4-(3-phenylmethoxy-4-methoxyphenyl)-1-(phenylmethyl)pyrrolidine:

46%; $^1$H-NMR (300 MHz): δ 2.65–3.06 (m, 5), 3.63 (s, 3), 3.85 (s, 3), 5.13 (s, 2).

(R). trans-3-(3-cyclopentoxy-4-methoxyphenyl)-4-(1,1-dimethylethoxycarbonyl)-1-(phenylmethyl)pyrrolidine:

88%. Anal. Calcd for $C_{28}H_{37}NO_4$: C, 74.47; H, 8.26; N, 3.10. Found: C, 74.29; H, 8.33; N, 3.06.

(S). 3-(3-cyclopentoxy-4-methoxyphenyl)-4-(1,1-dimethylethoxycarbonyl)-4-methyl-1-(phenylmethyl) pyrrolidine:

24%. Anal. Calcd for $C_{28}H_{37}NO_4$•0.5 $H_2O$: C, 73.39; H, 8.49; N, 2.95. Found: C, 73.36; H, 8.35; N, 2.99.

(T). trans-3-cyano-4-(3-cyclopentoxy-4-methoxyphenyl)-1-(phenylmethyl)pyrrolidine:

80%; $^1$H-NMR (300 MHz): δ 2.77–3.18 (m, 5), 3.70 (q, 2, J=13), 3.83 (s, 3), 6.80–7.37 (m, 8).

(U). trans-3-(3-cyclopentoxy-4-methoxyphenyl)-4-nitro-1-(phenylmethyl)pyrrolidine:

56%; $^1$H-NMR (300 MHz): δ 3.11–3.36 (m, 3), 3.82 (s, 3), 4.75 (m, 1), 4.88 (m, 1).

(V). 3-(3-cyclopentoxy-4-methoxyphenyl)-4-ethoxycarbonyl-4-methyl-1-(phenylmethyl)pyrrolidine: 87%.

(W). 3-(3-cyclopentoxy-4-methoxyphenyl)-4-methoxycarbonyl-4-methyl-1-(phenylmethyl)pyrrolidine:

99%. Anal. Calcd for $C_{26}H_{33}NO_4$: C, 73.73; H, 7.85; N, 3.31. Found: C, 73.46; H, 7.90; N, 3.28.

(X). 3-(3-Cyclopentoxy-4-methoxyphenyl)-3-methoxycarbonyl-1-(phenylmethyl)pyrrolidine To a solution of N-methoxymethyl-N-(phenylmethyl) trimethylsilylmethylamine (1.42 g, 6.0 mmol) and methyl 2-(3-cyclopentoxy-4-methoxyphenyl)prop-2-enoate (1.38 g, 5.0 mmol) in 10 mL of $CH_2Cl_2$ cooled to 0° C. was added a 0.7 mL of a 1M solution of trifluoroacetic acid. Stirring was continued for 12 hr, and the solution was partitioned between ether and sat. $NaHCO_3$. The layers were separated and the aqueous layer was extracted ethyl acetate (2×). The combined organic layers were dried ($K_2CO_3$), filtered, and concentrated under reduced pressure to a pale yellow oil. Chromatography on silica gel (3:1, hexanes:ethyl acetate) provided 3-(3-cyclopentoxy-4-methoxyphenyl)-3-methoxycarbonyl-1-(phenylmethyl)pyrrolidine (2.0 g, 99%) as a colorless oil. $^1$H-NMR (300 MHz): δ 2.75 (d, 1, J=9), 3.54 (d, 1, J=9), 3.67 (s, 3), 3.69 (s, 2), 3.81 (s, 3). Anal. Calcd for $C_{25}H_{31}NO_4$: C, 73.32; H, 7.63; N, 3.42. Found: C, 73.25; H, 7.65; N, 3.40.

(Y). trans-3-(3-Cyclopentoxy-4-methoxyphenyl)-4-phenylcarbonyl-1-(phenylmethyl)pyrrolidine To a solution of N-methoxymethyl-N-(phenylmethyl) trimethylsilylmethylamine (713 mg, 3.01 mmol) and (E)-3-(3-cyclopentoxy-4-methoxyphenyl)-1-phenylprop-2-enone (808 mg, 2.51 mmol) in 6 mL of $CH_2Cl_2$ cooled to 0° C. was added a 1 mL of a 1M solution of trifluoroacetic acid. Stirring was continued for 1 hr at 0° C. and 2 hr at room temperature. The solution was then partitioned between ether and sat. $NaHCO_3$. The layers were separated and the aqueous layer was extracted ethyl acetate (2×). The combined organic layers were dried ($K_2CO_3$), filtered, and concentrated under reduced pressure to a pale yellow oil. Chromatography on silica gel (3:1, hexanes:ethyl acetate) provided trans-3-(3-cyclopentoxy-4-methoxyphenyl)-4-phenylcarbonyl-1-(phenylmethyl)pyrrolidine (1.10 g, 96%) as a pale yellow oil. $^1$H-NMR (300 MHz): δ 2.81–3.25 (m, 4), 3.81 (s, 3), 3.97 (m, 1), 6.73–7.80 (m, 13).

The following compounds were prepared according to the general procedure as set forth above.

(Z). trans-3-(3-cyclopentoxy-4-methoxyphenyl)-4-ethylcarbonyl-1-(phenylmethyl)pyrrolidine:

95%; Anal. Calcd for $C_{26}H_{33}NO_3$: C, 76.63; H, 8.16; N, 3.44. Found: C, 76.58; H, 8.17; N, 3.39.

(AA). trans-3-(3-cyclopentoxy-4-methoxyphenyl)-4-methylcarbonyl-1-(phenylmethyl)pyrrolidine:

95%; $^1$H-NMR (300 MHz): δ 2.08 (s, 3), 2.71–3.20 (m, 5), 3.65 (q, 2, J=13), 3.82 (s, 3), 6.76–7.37 (m, 8).

(BB). trans-3-(Cyclopentoxy-4-methoxyphenyl)-4-(methoxycarbonyl)pyrrolidine trans-3-(3-Cyclopentoxy-4-methoxyphenyl)-4-methoxycarbonyl-1-(phenylmethyl)pyrrolidine (3.5 g, 8.6 mmol) was dissolved in 20 mL of 4% $HCO_2H$:methanol. While stirring at room temperature, 10% Pd/C (450 mg) was added in small portions. After several hours the reaction was diluted with methanol. Filtration through Celite followed by concentration under reduced pressure yielded a yellow oil residue. This residue was partitioned between $CH_2Cl_2$ and sat. $NaHCO_3$. The layers were separated and the aqueous layer was extracted with $CH_2Cl_2$ (2×). The organic layers were combined, dried ($K_2CO_3$), filtered, and concentrated under reduced pressure to afford a pale oil. Chromatography on silica gel (8:1:1, $CH_2Cl_2$:ethyl acetate:methanol) provided trans-3-(3-cyclopentoxy-4-methoxyphenyl)-4-(methoxycarbonyl)pyrrolidine as a colorless oil (2.3 g, 84%). $^1$H-NMR (300 MHz): δ 2.86–3.04 (m, 2), 3.29–3.52 (m, 4), 3.68 (s, 3), 3.83 (s, 3).

The following compounds were prepared according to the general procedure as set forth above.

(CC). trans-3-methoxycarbonyl-4-[3-(3-phenoxypropoxy)-4-methoxyphenyl]pyrrolidine:

82%; $^1$H-NMR (300 MHz): δ 2.31 (m, 1), 2.89–3.04 (m, 2), 3.31–3.51 (m, 4), 3.67 (s, 3), 3.83 (s, 3), 6.81–7.31 (m, 8).

(DD). 3-(3-cyclopentoxy-4-methoxyphenyl)-4-ethoxycarbonyl-4-methylpyrrolidine:

92%; $^1$H-NMR (300 MHz): δ 0.92 (s, 3), 2.87 (d, 1, J=11.7), 3.59 (d, 1, J=11.7), 3.83 (s, 3), 4.20 (q, 2, J=7.1), 6.71–6.82 (m, 3).

(EE). 3-(3-cyclopentoxy-4-methoxyphenyl)-4-methoxycarbonyl-4-methylpyrrolidine:

80%; $^1$H-NMR (300 MHz): δ 0.93 (s, 3), 2.88 (d, 1, J=12), 3.60 (d, 1, J=12), 3.75 (s, 3), 3.83 (s, 3), 6.71–6.82 (m, 3).

(FF). trans-3-(3-Cyclopentoxy-4-methoxyphenyl)-4-(hydroxymethyl)pyrrolidine

To a solution of trans-3-(3-cyclopentoxy-4-methoxyphenyl)-4-(methoxycarbonyl)pyrrolidine (500 mg, 1.57 mmol) in 7 mL of THF at 0° C. was added $LiAlH_4$ (60 mg, 1.57 mmol). The resulting mixture was stirred for 15 min at 0° C. and then allowed to stir at room temperature for 20 min. The mixture was then successively treated dropwise with $H_2O$ (0.06 mL), 15% NaOH (0.06 mL), and $H_2O$ (0.18 mL). The resulting suspension was then stirred for 1 hr, filtered through Celite, and concentrated under reduced pressure to an oil. Silica gel chromatography (1:1 CHCl$_3$:methanol) provided trans-3-(3-cyclopentoxy-4-methoxyphenyl)-4-(hydroxymethyl)pyrrolidine as a pale yellow oil (329 mg, 72%). $^1$H-NMR (300 MHz): δ 2.35 (m, 1), 2.90–3.08 (m, 3), 3.30–3.76 (m, 4), 3.82 (s, 3).

(GG). trans-3-(3-Cyclopentoxy-4-methoxyphenyl)-4-hydroxymethyl-1-(phenylmethyl)pyrrolidine To a solution of trans-3-(3-Cyclopentoxy-4-methoxyphenyl)-4-methoxycarbonyl-1-(phenylmethyl)pyrrolidine (2.7 g, 6.6 mmol) in 27 mL of THF at 0° C. was added LiAlH$_4$ (4.0 mmol, 4 mL of 1M toluene solution). After stirring for 2 hr the reaction mixture was then successively treated dropwise with H$_2$O (0.15 mL), 15% NaOH (0.15 mL), and H$_2$O (0.46 mL). The resulting suspension was diluted with ether, stirred for 1 hr, filtered through Celite, and concentrated under reduced pressure to an oil. Silica gel chromatography (graded elution: CH$_2$Cl$_2$ then 9:1, CH$_2$Cl$_2$:methanol) provided trans-3-(3-cyclopentoxy-4-methoxyphenyl)-4-hydroxymethyl-1-(phenylmethyl)pyrrolidine (2.0 g, 80%) as an oil.

EXAMPLES

Example 1 cis-3-(3-Cyclopentoxy-4-methoxyphenyl)-1-(1,1-dimethylethoxycarbonyl)-4-(methoxycarbonyl)pyrrolidine ($R^1$=cyclopentyl; $R^2$=H; $R^3$=—CO$_2$CH$_3$; $R^4$=H; $R^5$=—CO$_2$C(CH$_3$)$_3$; $R^{12}$=methyl)

cis-3-(3-Cyclopentoxy-4-methoxyphenyl)-4-methoxycarbonyl-1-(phenylmethyl)pyrrolidine (1.66 g, 4.1 mmol) was dissolved in 30 mL of 4% HCO$_2$H:methanol. While stirring at room temperature, 10% Pd/C (166 mg) was added in small portions. After 12 hr the reaction was diluted with methanol. Filtration through Celite followed by concentration under reduced pressure yielded a greenish oil residue, which was twice again concentrated from toluene. To this residue in 15 mL of CH$_2$Cl$_2$ at 0° C. was added 4-dimethylaminopyridine (650 mg, 5.33 mmol), followed by di-t-butyl-dicarbonate (1.07 g, 4.92 mmol). The bath was removed, and the mixture was stirred at room temperature. After 45 min the reaction mixture was diluted with CH$_2$Cl$_2$, washed with 1M H$_3$PO$_4$, dried over MgSO$_4$, filtered, and concentrated under reduced pressure. Silica gel chromatography (2:1, hexanes:ethyl acetate) provided cis-3-(3-cyclopentoxy-4-methoxyphenyl)-1-(1,1-dimethylethoxycarbonyl)-4-(methoxycarbonyl)pyrrolidine as a colorless oil (1.1 g, 64%), m.p. 85°–87° C. $^1$H-NMR (300 MHz): δ 1.50 (s, 9), 3.44 (s, 3), 3.82 (s, 3), 4.72 (bs, 1). Anal. Calcd for C$_{23}$H$_{33}$NO$_6$: C, 65.85; H, 7.93; N, 3.34. Found: C, 65.93; H, 7.95; N, 3.32.

The following compounds were prepared according to the general procedure set forth above in Example 1:

Example 2 trans-3-(3-cyclopentoxy-4-methoxyphenyl)-1-(1,1-dimethylethoxycarbonyl)-4-(methoxycarbonyl)pyrrolidine ($R^1$=cyclopentyl; $R^2$=H; $R^3$=—CO$_2$CH$_3$; $R^4$=H; $R^5$=—CO$_2$C(CH$_3$)$_3$; $R^{12}$=methyl)

38%; $^1$H-NMR (300 MHz): δ 1.48 (s, 9), 3.64 (s, 3), 3.83 (s, 3), 4.76 (bs, 1). Anal. Calcd for C$_{23}$H$_{33}$NO$_6$: C, 65.85; H, 7.93; N, 3.34. Found: C, 65.73; H, 7.93; N, 3.29.

Example 3 trans-3-methoxycarbonyl-1-(1,1-dimethylethoxycarbonyl)-4-[3-(3-phenoxypropoxy)-4-methoxyphenyl]pyrrolidine ($R^1$=phenoxypropyl; $R^2$=H; $R^3$=—CO$_2$CH$_3$; $R^4$=H; $R^5$=—CO$_2$C(CH$_3$)$_3$; $R^{12}$=methyl)

42%; Anal. Calcd for C$_{27}$H$_{35}$NO$_7$: C, 66.79; H, 7.27; N, 2.89. Found: C, 66.63; H, 7.33; N, 2.80.

Example 4 trans-3-(3,4-dimethoxyphenyl)-1-(1,1-dimethylethoxycarbonyl)-4-(methoxycarbonyl)pyrrolidine ($R^1$=methyl; $R^2$=H; $R^3$=—CO$_2$CH$_3$; $R^4$=H; $R^5$=—CO$_2$C(CH$_3$)$_3$; $R^{12}$=methyl)

71%; Anal. Calcd. for C$_{19}$H$_{27}$NO$_6$: C, 62.45; H, 7.45; N, 3.83. Found: C, 62.24; H, 7.48; N, 3.81.

Example 5

3-(3-Cyclopentoxy-4-methoxyphenyl)-1-(1,1-dimethylethoxycarbonyl)-3-(methoxycarbonyl)pyrrolidine ($R^1$=cyclopentyl; $R^2$=—CO$_2$CH$_3$; $R^3$=H; $R^4$=H; $R^5$=—CO$_2$C(CH$_3$)$_3$; $R^{12}$=methyl)

3-(3-Cyclopentoxy-4-methoxyphenyl)-3-methoxycarbonyl-1-(phenylmethyl)pyrrolidine (1.6 g, 3.9 mmol) was dissolved in 40 mL of 4% HCO$_2$H:methanol. While stirring at room temperature, 10% Pd/C (160 mg) was added in small portions. After 12 hr the reaction was diluted with methanol. Filtration through Celite followed by concentration under reduced pressure yielded a greenish oil residue, which was twice again concentrated from toluene. To this residue in 10 mL of CH$_2$Cl$_2$ at 0° C. was added 4-dimethylaminopyridine (620 mg, 5.0 mmol), followed by di-t-butyl-dicarbonate (1.02 g, 4.7 mmol). The bath was removed, and the mixture was stirred at room temperature. After 3 hr the reaction mixture was diluted with CH$_2$Cl$_2$, washed with 1M H$_3$PO$_4$, dried over MgSO$_4$, filtered, and concentrated under reduced pressure. Silica gel chromatography (5:1, hexanes:ethyl acetate) provided 3-(3-cyclopentoxy-4-methoxyphenyl)-1-(1,1-dimethylethoxycarbonyl)-3-(methoxycarbonyl)pyrrolidine as a colorless oil (1.2 g, 70%). $^1$H-NMR indicates a 1:1 mixture of rotamers. Anal. Calcd for C$_{23}$H$_{33}$NO$_6$: C, 65.85; H, 7.93; N, 3.34. Found: C, 65.66; H, 8.01; N, 3.26.

Example 6 trans-3-(3-Cyclopentoxy-4-methoxyphenyl)-1-(1,1-dimethylethoxycarbonyl)-4-(hydroxymethyl)pyrrolidine ($R^1$=cyclopentyl; $R^2$=H; $R^3$=CH$_2$OH; $R^4$=H; $R^5$=—CO$_2$C(CH$_3$)$_3$; $R^{12}$=methyl)

trans-3-(3-Cyclopentoxy-4-methoxyphenyl)-4-hydroxymethyl-1-(phenylmethyl)pyrrolidine (200 mg, 0.53 mmol) was dissolved in 5 mL of 4% HCO$_2$H:methanol. While stirring at room temperature, 10% Pd/C (30 mg) was added. After 4 hr the reaction was diluted with methanol. Filtration through Celite followed by concentration under reduced pressure yielded an oil residue. To this residue dissolved in 2 mL of CH$_2$Cl$_2$ at 0° C. was added 4-dimethylaminopyridine (64 mg, 0.5 mmol), followed by di-t-butyl-dicarbonate (126 mg, 0.58 mmol). The bath was removed, and the mixture was stirred at room temperature for 15 hr. The reaction mixture was then diluted with $CH_2Cl_2$, washed with 1M $H_3PO_4$, dried over $MgSO_4$, filtered, and concentrated under reduced pressure. Silica gel chromatography (1:1, hexanes:ethyl acetate) provided 3-(3-cyclopentoxy-4-methoxyphenyl)-1-(1,1-dimethylethoxycarbonyl)-4-(hydroxymethyl)pyrrolidine as a colorless oil (130 mg, 63%). Anal. Calcd for $C_{22}H_{33}NO_5$: C, 67.49; H, 8.49; N, 3.58. Found: C, 67.23; H, 8.58; N, 3.49.

Example 7 trans-3-(3-Cyclopentoxy-4-methoxyphenyl)-4-hydroxymethyl-1-(methoxycarbonyl)pyrrolidine ($R^1$=cyclopentyl; $R^2$=H; $R^3$=$CH_2OH$; $R^4$=H; $R^5$=—$CO_2CH_3$; $R^{12}$=methyl)

To a vigorously stirring mixture of 3-(3-cyclopentoxy-4-methoxyphenyl)-4-(hydroxymethyl)pyrrolidine (328 mg, 1.13 mmol) in 4 mL of 1:1 ethyl acetate:sat aq $NaHCO_3$ was added methyl chloroformate (138 mg, 1.47 mmol). When TLC analysis indicated a complete reaction the mixture was diluted with ethyl acetate, and the layers were separated. The organic layer was dried over $K_2CO_3$, filtered, and concentrated under reduced pressure to provide 3-(3-cyclopentoxy-4-methoxyphenyl)-4-hydroxymethyl-1-(methoxycarbonyl)pyrrolidine as a colorless viscous oil (273 mg, 69%). Anal. Calcd for $C_{19}H_{27}NO_5 \cdot 0.5 H_2O$: C, 63.67; H, 7.87; N, 3.91. Found: C, 63.30; H, 7.75; N, 3.92.

Example 8 trans-1-Aminocarbonyl-3-(3-Cyclopentoxy-4-methoxyphenyl)-4-(methoxycarbonyl)pyrrolidine ($R^1$=cyclopentyl; $R^2$=H; $R^3$=—$CO_2CH_3$; $R^4$=H; $R^5$=—$CONH_2$; $R^{12}$=methyl)

To a solution of trans-3-(3-cyclopentoxy-4-methoxyphenyl)-1-(1,1-dimethylethoxycarbonyl)-4-(methoxycarbonyl)pyrrolidine (419 mg, 1.0 mmol) in 2 mL of $CH_2Cl_2$ at 0° C. was added 2.3 mL of trifluoroacetic acid. The solution was stirred for 12 hr at room temperature, and concentrated to an oil. The oil was dissolved in 2 mL of $CH_2Cl_2$ and 4-dimethylaminopyridine 366 mg, 3.0 mmol) was added. To this solution at 0° C. was added trimethylsilylisocyanate (1.15 g, 10.0 mmol). The bath was removed and the resulting mixture was allowed to stir for 60 hr. After dilution with $CH_2Cl_2$, the reaction mixture was washed with 1M $H_3PO_4$ and brine. The organic layer was dried over $MgSO_4$, filtered, and concentrated under reduced pressure. Silica gel chromatography (9:1, $CH_2Cl_2$:methanol) provided a foam. Crystallization with diisopropyl ether afforded trans-1-aminocarbonyl-3-(3-cyclopentoxy-4-methoxyphenyl)-4-(methoxycarbonyl)pyrrolidine as a white solid (243 mg, 67%), m.p. 127°–129° C. Anal. Calcd for $C_{19}H_{26}N_2O_5$: C, 62.97; H, 7.23; N, 7.73. Found: C, 63.07; H, 7.23; N, 7.76.

The following compounds were prepared according to the general procedure set forth above in Example 8:

Example 9 cis-1-aminocarbonyl-3-(3-cyclopentoxy-4-methoxyphenyl)-4-(methoxycarbonyl)pyrrolidine:

($R^1$=cyclopentyl; $R^2$=H; $R^3$=—$CO_2CH_3$; $R^4$=H; $R^5$=—$CONH_2$; $R^{12}$=methyl)

81%; m.p. 133°–35° C. Anal. Calcd for $C_{19}H_{26}N_2O_5$: C, 62.97; H, 7.23; N, 7.73. Found: C, 62.82; H, 7.27; N, 7.71.

Example 10

1-aminocarbonyl-3-(3-cyclopentoxy-4-methoxyphenyl)-3-(methoxycarbonyl)pyrrolidine:

($R^1$=cyclopentyl; $R^2$=—$CO_2CH_3$; $R^3$=H; $R^4$=H; $R^5$=—$CONH_2$; $R^{12}$=methyl)

95%: $^1$H-NMR (300 MHz): δ 2.94 (m, 1), 3.38–3.59 (m, 2), 3.67 (s, 3), 3.84 (s, 3), 6.83 (s, 3). Anal. Calcd for $C_{19}H_{26}N_2O_5$: C, 62.97; H, 7.23; N, 7.73. Found: C, 62.87; H, 7.27; N, 7.66.

Example 11 trans-1- Methoxycarbonyl-3-methoxycarbonyl-4-(3-phenylmethoxy-4-methoxyphenyl)pyrrolidine ($R^1$=—$CH_2$-(phenyl); $R^2$=H; $R^3$=—$CO_2CH_3$; $R^4$=H; $R^5$=—$CO_2CH_3$; $R^{12}$=methyl)

To a solution of 3-methoxycarbonyl-4-[3-(3-phenylmethoxy)-4-methoxyphenyl]-1-(phenylmethyl)pyrrolidine (3.0 g, 6.95 mmol) in 14 mL of $CH_3CN$ was added methyl chloroformate (1.31 g, 13.9 mmol). The resulting solution was heated to reflux. After 1.5 hr an additional 650 mg of methyl chloroformate was added. After 4 hr the solution was concentrated. Silica gel chromatography of the residue (2:1, hexanes:ethyl acetate) yielded trans-1-methoxycarbonyl-3-methoxycarbonyl-4-(3-phenylmethoxy-4-methoxyphenyl)pyrrolidine as a cloudy, colorless oil (2.61 g, 94%). Anal. Calcd for $C_{22}H_{25}NO_6$: C, 66.15; H, 6.31; N, 3.51. Found: C, 65.92; H, 6.38; N, 3.41.

The following compounds were prepared according to the general procedure set forth above in Example 11:

Example 12 trans-3-(3-cyclopentoxy-4-methoxyphenyl)-1-methoxycarbonyl-4-methyl-4-(methycarbonyl) pyrrolidine:

($R^1$=cyclopentyl; $R^2$=H; $R^3$=—$CH_3$; $R^4$=—$COCH_3$; $R^5$=—$CO_2CH_3$; $R^{12}$=methyl)

64% Anal. Calcd for $C_{21}H_{29}NO_5$: C, 67.18; H, 7.79; N, 3.73. Found: C, 67.00; H, 7.78; N, 3.66.

Example 13 trans-3-(3-cyclopentoxy-4-methoxyphenyl)-4-(1,1-dimethylethoxycarbonyl)-1-(methoxycarbonyl) pyrrolidine:

($R^1$=cyclopentyl; $R^2$=H; $R^3$=—$CO_2C(CH_3)_3$; $R^4$=H; $R^5$=—$CO_2CH_3$; $R^{12}$=methyl)

80%; Anal. Calcd for $C_{23}H_{33}NO_6$: C, 65.85; H, 7.93; N, 3.34. Found: C, 65.73; H, 8.03; N, 3.27.

Example 14

3-(3-cyclopentoxy-4-methoxyphenyl)-4-(1,1-dimethylethoxycarbonyl)-1-methoxycarbonyl-4-methylpyrrolidine:

($R^1$=cyclopentyl; $R^2$=H; $R^3$=—$CO_2C(CH_3)_3$; $R^4$=—$CH_3$; $R^5$=—$CO_2CH_3$; $R^{12}$=methyl)

79%; Anal. Calcd for $C_{24}H_{35}NO_6 \cdot 0.5 H_2O$: C, 65.14; H, 8.20; N, 3.17. Found: C, 65.11; H, 8.00; N, 3.13.

Example 15 trans-3-(3-cyclopentoxy-4-methoxyphenyl)-4-ethylcarbonyl-1-(methoxycarbonyl)pyrrolidine:

($R^1$=cyclopentyl; $R^2$=H; $R^3$=—COCH$_2$CH$_3$; $R^4$=H; $R^5$=—CO$_2$CH$_3$; $R^{12}$=methyl)

67%; Anal. Calcd for $C_{21}H_{29}NO_5$: C, 67.18; H, 7.79; N, 3.73. Found: C, 67.14; H, 7.86; N, 3.73.

Example 16 trans-1-methoxycarbonyl-3-nitro-4-[3-(3-phenoxypropoxy)-4-methoxyphenyl]pyrrolidine:

26%; Anal. Calcd for $C_{22}H_{26}N_2O_7$: C, 61.39; H, 6.09; N, 6.51. Found: C, 61.23; H, 6.16; N, 6.43.

($R^1$=phenoxypropyl; $R^2$=H; $R^3$=—NO$_2$; $R^4$=—CH$_3$; $R^5$=—CO$_2$CH$_3$; $R^{12}$=methyl)

Example 17 trans-3-Cyano-4-(3-cyclopentoxy-4-methoxyphenyl)-1-(methoxycarbonyl)pyrrolidine ($R^1$=cyclopentyl; $R^2$=H; $R^3$=—CN; $R^4$=H; $R^5$=—CO$_2$CH$_3$; $R^{12}$=methyl To a solution of 3-cyano-4-(3-cyclopentoxy-4-methoxyphenyl)-1-(phenylmethyl)pyrrolidine (300 mg, 0.79 mmol) in 2 mL of CH$_3$CN in a thick-walled glass sealable tube was added methyl chloroformate (300 mg, 3.19 mmol). The tube was sealed and the resulting solution was heated to 80° C. for 12 hr. After cooling to room temperature, the solution was concentrated. Silica gel chromatography of the residue (2:1, hexanes:ethyl acetate) provided trans-3-cyano-4-(3-cyclopentoxy-4-methoxyphenyl)-1-(methoxycarbonyl)pyrrolidine as a white solid (233 mg, 85%), m.p. 101°–104° C. Anal. Calcd for $C_{19}H_{24}N_2O_4$: C, 66.26; H, 7.02; N, 8.13. Found: C, 66.14; H, 7.06; N, 8.10.

The following compound was prepared according to the general procedure set forth above in Example 17:

Example 18 trans-3-(3-cyclopentoxy-4-methoxyphenyl)-1-methoxycarbonyl-4-nitropyrrolidine:

($R^1$=cyclopentyl; $R^2$=H; $R^3$=—NO$_2$; $R^4$=H; $R^5$=—CO$_2$CH$_3$; $R^{12}$=methyl)

$^1$H-NMR (300 MHz): δ 3.76 (s, 3), 3.82 (s, 3), 4.73 (m, 1), 4.93 (m, 1). Anal. Calcd for $C_{18}H_{24}N_2O_6$: C, 59.33; H, 6.68; N, 7.69. Found: C, 59.28; H, 6.66; N, 7.62.

Example 19 trans-3-(3-Cyclopentoxy-4-methoxyphenyl)-1-methoxycarbonyl-4-(methylcarbonyl)pyrrolidine ($R^1$=cyclopentyl; $R^2$=H; $R^3$=—COCH$_3$; $R^4$=H; $R^5$=—CO$_2$CH$_3$; $R^{12}$=methyl)

To a solution of trans-3-(3-cyclopentoxy-4-methoxyphenyl)-4-methylcarbonyl-1-(phenylmethyl)pyrrolidine (703 mg, 1.78 mmol) in 3.5 mL of dichloroethane in a thick-walled glass sealable tube was added methyl chloroformate (336 mg, 3.56 mmol). The tube was sealed and the resulting solution was heated to 80° C. for 8 hr. After cooling to room temperature, the solution was concentrated. Silica gel chromatography of the residue (6:3:1, hexanes:ethyl acetate:CH$_2$Cl$_2$) provided trans-3-(3-cyclopentoxy-4-methoxyphenyl)-1-methoxycarbonyl-4-(methylcarbonyl)pyrrolidine as a viscous oil (350 mg, 54%). Anal. Calcd for $C_{20}H_{27}NO_5$: C, 66.46; H, 7.53; N, 3.88. Found: C, 66.24; H, 7.60; N, 3.79.

The following compound was prepared according to the general procedure set forth above in Example 19:

Example 20 trans-3-(3-cyclopentoxy-4-methoxyphenyl)-1-methoxycarbonyl-4-(phenylcarbonyl)pyrrolidine:

($R^1$=cyclopentyl; $R^2$=H; $R^3$=phenylcarbonyl; $R^4$=H; $R^5$=—CO$_2$CH$_3$; $R^{12}$=methyl)

59%; Anal. Calcd for $C_{25}H_{29}NO_5$: C, 70.90; H, 6.90; N, 3.31. Found: C, 70.72; H, 6.95; N, 3.25.

Example 21 trans-1-Methoxycarbonyl-3-methoxycarbonyl-4-[3-(3-phenoxypropoxy)-4-methoxyphenyl]pyrrolidine ($R^1$=phenoxypropyl; $R^2$=H; $R^3$=—CO$_2$CH$_3$; $R^4$=H; $R^5$=—CO$_2$CH$_3$; $R^{12}$=methyl)

To a solution of 3-methoxycarbonyl-4-[3-(3-phenoxypropoxy)-4-methoxyphenyl]pyrrolidine (720 mg, 1.87 mmol) in 5 mL of CH$_2$Cl$_2$ at 0° C. was added DMAP (275 mg, 2.25 mmol), followed by methyl chloroformate (213 mg, 2.25 mmol). The solution was stirred for 2 hr, diluted with ether, and washed with 1M H$_3$PO$_4$. The aqueous layer was extracted with ether (2×) and ethyl acetate (1×). The combined organic layers were dried over MgSO$_4$, filtered and concentrated to a colorless oil. Silica gel chromatography (4:2:1, hexanes:ethyl acetate:CH$_2$Cl$_2$) provided trans-1-methoxycarbonyl-3-methoxycarbonyl-4-[3-(3-phenoxypropoxy)-4-methoxyphenyl]pyrrolidine as a colorless oil (634 mg, 77%). Anal. Calcd for $C_{24}H_{29}NO_7$: C, 64.99; H, 6.59; N, 3.16. Found: C, 64.85; H, 6.57; N, 3.15.

The following compounds were prepared according to the general procedure set forth above in Example 21:

Example 22

3-(3-cyclopentoxy-4-methoxyphenyl)-4-ethoxycarbonyl-1-methoxycarbonyl-4-methylpyrrolidine:

($R^1$=cyclopentyl; $R^2$=H; $R^3$=—CO$_2$CH$_2$CH$_3$; $R^4$=—CH$_3$; $R^5$=—CO$_2$CH$_3$; $R^{12}$=methyl)

85%; Anal. Calcd for $C_{22}H_{31}NO_6$: C, 65.17; H, 7.71; N, 3.45. Found: C, 65.19; H, 7.71; N, 3.35

Example 23

3-(3-cyclopentoxy-4-methoxyphenyl)-1-methoxycarbonyl-4-methoxycarbonyl-4-methylpyrrolidine:

($R^1$=cyclopentyl; $R^2$=H; $R^3$=—CO$_2$CH$_2$CH$_3$; $R^4$=—CH$_3$; $R^5$=—CO$_2$CH$_3$; $R^{12}$=methyl)

75%; Anal. Calcd for $C_{21}H_{29}NO_6$: C, 64.43; H, 7.47; N, 3.58. Found: C, 63.64; H, 7.48; N, 3.54.

Example 24 trans-3-(3-cyclopentoxy-4-methoxyphenyl)-1-methoxycarbonyl-4-(methoxycarbonyl)pyrrolidine:

($R^1$=cyclopentyl; $R^2$=H; $R^3$=—CO$_2$CH$_3$; $R^4$=H; $R^5$=—CO$_2$CH$_3$; $R^{12}$=methyl)

96%; $^1$H-NMR (300 MHz): δ 3.65 (s, 3), 3.73 (s, 3), 3.82 (s, 3).

Example 25 trans-3-(3-Cyclopentoxy-4-methoxyphenyl)-4-methoxycarbonyl-1-(methylcarbonyl)pyrrolidine ($R^1$=cyclopentyl; $R^2$=H; $R^3$=—$CO_2CH_3$; $R^4$=H; $R^5$=—$COCH_3$; $R^{12}$=methyl)

To a solution of trans-3-(3-cyclopentoxy-4-methoxyphenyl)-4-(methoxycarbonyl)pyrrolidine (605 mg, 1.89 mmol) in 5 mL of $CH_2Cl_2$ was added 4-dimethylaminopyridine (347 mg, 2.84 mmol), followed by 1 mL of acetic anhydride After 12 hr the reaction was diluted with $CH_2Cl_2$ and washed with 1M $H_3PO_4$. The organic layer was dried over $MgSO_4$, filtered, and concentrated under reduced pressure. Silica gel chromatography (2:1, hexanes:ethyl acetate) provided trans-3-(3-cyclopentoxy-4-methoxyphenyl)-4-methoxycarbonyl-1-(methylcarbonyl)pyrrolidine as a viscous oil (370 mg, 54%). $^1$H-NMR (300 MHz) analysis indicates a 1:1 mixture of amide rotamers (δ 2.07 and 2.09 singlets). Anal. Calcd for $C_{20}H_{27}NO_5$: C, 66.46; H, 7.53; N, 3.88. Found: C, 66.19; H, 7.58; N, 3.82.

Example 26 trans-3-(3-Cyclopentoxy-4-methoxyphenyl)-1-ethylcarbonyl-4-(methoxycarbonyl)pyrrolidine ($R^1$=cyclopentyl; $R^2$=H; $R^3$=—$CO_2CH_3$; $R^4$=H; $R^5$=—$COCH_2CH_3$; $R^{12}$=methyl)

To a solution of trans-3-(3-cyclopentoxy-4-methoxyphenyl)-4-(methoxycarbonyl)pyrrolidine (300 mg, 0.94 mmol) in 3 mL of $CH_2Cl_2$ at 0° C. was added 4-dimethylaminopyridine (149 mg, 1.22 mmol), followed by propionic anhydride (135 mg, 1.03 mmol). After 5 hr the reaction was diluted with $CH_2Cl_2$ and washed with 1M $H_3PO_4$. The organic layer was dried over $MgSO_4$, filtered, and concentrated under reduced pressure. Silica gel chromatography (1:1, hexanes:ethyl acetate) provided trans-3-(3-cyclopentoxy-4-methoxyphenyl)-1-ethylcarbonyl-4-(methoxycarbonyl)pyrrolidine as a viscous oil (197 mg, 56%). Anal. Calcd for $C_{21}H_{29}NO_5$•0.25 $H_2O$: C, 66.38; H, 7.83; N, 3.69. Found: C, 66.48; H, 7.87; N, 3.65.

Example 27 trans-3-(3-Cyclopentoxy-4-methoxyphenyl)-1-(1-imidazolylcarbonyl)-4-(methoxycarbonyl)pyrrolidine ($R^1$=cyclopentyl; $R^2$=H; $R^3$=—$CO_2CH_3$; $R^4$=H; $R^5$=imidazolylcarbonyl; $R^{12}$=methyl)

To a solution of trans-3-(3-cyclopentoxy-4-methoxyphenyl)-4-(methoxycarbonyl)pyrrolidine (400 mg, 1.25 mmol) in 3 mL of $CH_2Cl_2$ cooled to 0° C. was added 1,1'-carbonyldiimidazole (223 mg, 1.38 mmol). After 30 min the reaction was diluted with $CH_2Cl_2$ and washed with $H_2O$. The organic layer was dried over $K_2CO_3$, filtered, and concentrated under reduced pressure. Silica gel chromatography of the foamy solid (9:1, $CH_2Cl_2$:methanol) provided trans-3-(3-cyclopentoxy-4-methoxyphenyl)-1-imidazolylcarbonyl-4-(methoxycarbonyl)pyrrolidine as a white solid (504 mg, 97%), m.p. 40°–45° C. Anal. Calcd for $C_{22}H_{27}N_3O_5$: C, 63.91; H, 6.58; N, 10.16. Found: C, 63.11; H, 6.60; N, 10.09.

Example 28 trans-3-(3-Cyclopentoxy-4-methoxyphenyl)-1-formyl-4-(methoxycarbonyl)pyrrolidine ($R^1$=cyclopentyl; $R^2$=H; $R^3$=—$CO_2CH_3$; $R^4$=H; $R^5$=—CHO; $R^{12}$=methyl)

A solution of trans-3-(3-cyclopentoxy-4-methoxyphenyl)-4-(methoxycarbonyl)pyrrolidine (620 mg, 1.94 mmol) in 5 mL of ethyl formate was heated at reflux for 3 hr. The reaction was diluted with ether and concentrated. The residue was dissolved in ether and washed with 1M $H_3PO_4$. The organic layer was dried over $MgSO_4$, filtered, and concentrated under reduced pressure. Silica gel chromatography (2:1, ethyl acetate:hexanes) provided trans-3-(3-cyclopentoxy-4-methoxyphenyl)-1-formyl-4-(methoxycarbonyl)pyrrolidine as a colorless oil (567 mg, 84%). $^1$H-NMR (300 MHz): δ 3.11–3.21 (1, m), 3.65 (s, 3), 3.82 (s, 3), 6.73–6.82 (m, 3), 8.26 (s, 1).

The following compound was prepared according to the general procedure set forth above in Example 28:

Example 29 trans-1-formyl-3-methoxycarbonyl-4-[3-(3-phenoxypropoxy)-4-methoxyphenyl]pyrrolidine:

($R^1$=phenoxypropyl; $R^2$=H; $R^3$=—$CO_2CH_3$; $R^4$=H; $R^5$=—CHO; $R^{12}$=methyl)

Anal. Calcd for $C_{23}H_{27}NO_6$: C, 66.81; H, 6.58; N, 3.39. Found: C, 66.72; H, 6.59; N, 3.41.

Example 30 trans-3-(3-Cyclopentoxy-4-methoxyphenyl)-1-methoxycarbonyl-4-(1-(methylethoxycarbonyl)pyrrolidine ($R^1$=cyclopentyl; $R^2$=H; $R^3$=—$CO_2CH(CH_3)_2$; $R^4$=H; $R^5$=—$CO_2CH_3$; $R^{12}$=methyl)

To a solution of trans-3-carboxy-4-[(3-cyclopentoxy-4-methoxy)phenyl]-1-(methoxycarbonyl)pyrrolidine (200 mg, 0.55 mmol) in 3 mL of 2-propanol was added drops of concentrated $H_2SO_4$, and the solution was heated to reflux for 36 hr. The solution was cooled to room temperature, diluted with $CH_2Cl_2$ and washed with sat. $NaHCO_3$. The organic layer was dried over $MgSO_4$, filtered, and concentrated under reduced pressure to a yellow oil. Silica gel chromatography (3:1, hexanes:ethyl acetate) provided trans-3-(3-cyclopentoxy-4-methoxyphenyl)-1-methoxycarbonyl-4-(methylethoxycarbonyl)pyrrolidine as a viscous, pale yellow oil (126 mg, 56%). Anal. Calcd for $C_{22}H_{31}NO_6$: C, 65.17; H, 7.71; N, 3.45. Found: C, 64.89; H, 7.73; N, 3.38.

Example 31 trans-3-(3-Cyclopentoxy-4-methoxyphenyl)-4-ethoxycarbonyl-1-(methoxycarbonyl)pyrrolidine ($R^1$=cyclopentyl; $R^2$=H; $R^3$=—$CO_2CH_2CH_3$; $R^4$=H; $R^5$=—$CO_2CH_3$; $R^{12}$=methyl)

To a solution of trans-3-carboxy-4-[(3-cyclopentoxy-4-methoxy)phenyl]-1-(methoxycarbonyl)pyrrolidine (300 mg, 0.83 mmol) in 5 mL of ethanol was added 2 drops of concentrated $H_2SO_4$, and the solution was heated to reflux for 3 hr. The solution was cooled to room temperature and concentrated under reduced pressure. The residue was dissolved in $CH_2Cl_2$ and washed with sat. $NaHCO_3$. The organic layer was dried over $MgSO_4$, filtered, and concentrated under reduced pressure to a yellow oil. Silica gel chromatography (2:1, hexanes:ethyl acetate) provided trans-3-(3-cyclopentoxy-4-m ethoxyphenyl)-4-ethoxycarbonyl-1-(methoxycarbonyl)pyrrolidine as a pale yellow oil (200 mg, 62%). Anal. Calcd for $C_{21}H_{29}NO_6$: C, 64.43; H, 7.47; N, 3.58. Found: C, 64.37; H, 7.51; N, 3.52.

Example 32 trans-3-Carboxy-4-(3-cyclopentoxy-4-methoxyphenyl)-1-(1,1-dimethylethoxycarbonyl)pyrrolidine ($R^1$=cyclopentyl; $R^2$=H; $R^3$=—COOH; $R^4$=H; $R^5$=—$CO_2C(CH_3)_3$; $R^{12}$=methyl)

To a solution of trans-3-(3-cyclopentoxy-4-methoxyphenyl-1-(1,1-dimethylethoxycarbonyl)-4-(methoxycarbonyl)pyrrolidine (680 mg, 1.63 mmol) in 2 mL of 1,4-dioxane at 0° C. was added LiOH•$H_2O$ (82 mg, 1.96 mmol) dissolved in 5 mL of $H_2O$. Stirring was continued at 0° C. for 1 hr, at which time the resulting solution was diluted with ether and poured into 1M $H_3PO_4$. The aqueous layer was extracted with ether (3×), washed with brine, dried ($MgSO_4$), filtered, and concentrated under reduced pressure to give trans-3-carboxy-4-[(3-cyclopentoxy-4-methoxy)phenyl]-1-(1,1-dimethylethoxycarbonyl)pyrrolidine, which solidified to a colorless foamy solid under high vacuum (640 mg, 94%). Anal. Calcd for $C_{22}H_{31}NO_6$: C, 65.17; H, 7.71; N, 3.45. Found: C, 65.11; H, 7.87; N, 3.28.

The following compounds were prepared according to the general procedure set forth above in Example 32:

Example 33 trans-3-carboxy-4-(3-cyclopentoxy-4-methoxyphenyl)-1-(methoxycarbonyl)pyrrolidine:

($R^1$=cyclopentyl; $R^2$=H; $R^3$=—COOH; $R^4$=H; $R^5$=—$CO_2CH_3$; $R^{12}$=methyl)

83%; $^1$H-NMR (300 MHz): δ 3.13 (m, 1), 3.72 (s, 3), 3.82 (s, 3), 6.76–6.83 (m, 3).

Example 34 trans-3-carboxy-4-(3-cyclopentoxy-4-methoxyphenyl)-1-(phenylmethoxycarbonyl)pyrrolidine:

($R^1$=cyclopentyl; $R^2$=H; $R^3$=—COOH; $R^4$=H; $R^5$=—$CO_2CH_2$-phenyl; $R^{12}$=methyl)

91%; Anal. Calcd for $C_{25}H_{29}NO_6$: C, 68.32; H, 6.65; N, 3.19. Found: C, 68.04; H, 6.79; N, 3.01.

Example 35 trans-3-carboxy-4-(3-cyclopentoxy-4-methoxyphenyl)-1-(1-methylethoxycarbonyl)pyrrolidine:

($R^1$=cyclopentyl; $R^2$=H; $R^3$=—COOH; $R^4$=H; $R^5$=—$CO_2CH(CH_3)_2$; $R^{12}$=methyl)

80%; $^1$H-NMR (300 MHz): δ 1.26 (bs, 6), 3.82 (s, 3), 4.94 (m, 1), 6.73–6.83 (m, 3).

Example 36 trans-3-carboxy-1-methoxycarbonyl-4-[8-(3-phenoxypropoxy)-4-methoxyphenyl]pyrrolidine:

($R^1$=phenoxypropyl; $R^2$=H; $R^3$=—COOH; $R^4$=H; $R^5$=—$CO_2CH_3$; $R^{12}$=methyl)

89%; Anal. Calcd for $C_{23}H_{27}NO_7$•0.25 $H_2O$: C, 63.66; H, 6.39; N, 3.23. Found: C, 63.77; H, 6.65; N, 3.21.

Example 37 trans-3-carboxy-4-(3-cyclopentoxy-4-methoxyphenyl)-1-formylpyrrolidine:

($R^1$=cyclopentyl; $R^2$=H; $R^3$=—COOH; $R^4$=H; $R^5$=—CHO; $R^{12}$=methyl)

Anal. Calcd for $C_{18}H_{23}NO_5$: C, 64.85; H, 6.95; N, 4.20. Found: C, 64.76; H, 6.93; N, 4.09.

Example 38 trans-1-aminocarbonyl-3-carboxy-4-(3-cyclopentoxy-4-methoxyphenyl)pyrrolidine:

($R^1$=cyclopentyl; $R^2$=H; $R^3$=—COOH; $R^4$=H; $R^5$=—$CONH_2$; $R^{12}$=methyl)

68%; m.p. 199°–209° C.

Example 39 trans-3-Aminocarbonyl-4-(3-cyclopentoxy-4-methoxyphenyl)-1-(methoxycarbonyl)pyrrolidine ($R^1$=cyclopentyl; $R^2$=H; $R^3$=—$CONH_2$; $R^4$=H; $R^5$=—$CO_2CH_3$; $R^{12}$=methyl)

To a solution of trans-3-carboxy-4-(3-cyclopentoxy-4-methoxyphenyl)-1-(methoxycarbonyl)pyrrolidine (1.5 g, 4.1 mmol) in 11 mL of $CH_2Cl_2$ at 0° C. was added 1,1'-carbonyldiimidazole (736 mg, 4.5 mmol) in portions. The cooling bath was removed, and the solution was stirred at room temperature for 20 min. Ammonia gas was passed over the stirring solution for 4 min, and stirring was continued an additional 15 min. The solution was diluted with $CH_2Cl_2$ and poured into 1M $H_3PO_4$. The aqueous layer was extracted with $CH_2Cl_2$ (2×), and the combined organic layers were washed with brine, dried ($MgSO_4$), filtered, and concentrated under reduced pressure to a pale yellow foam. Silica gel chromatography (8:1:1, $CH_2Cl_2$:ethyl acetate:methanol) provided trans-3-aminocarbonyl-4-(3-cyclopentoxy-4-methoxyphenyl)-I-(methoxycarbonyl)pyrrolidine as a white solid (1.1 g, 76%), m.p. 130°–32° C. Anal. Calcd for $C_{19}H_{26}N_2O_5$: C, 62.97; H, 7.23; N, 7.73. Found: C, 63.03; H, 7.28; N, 7.65.

Example 40 trans-3-Aminocarbonyl-4-(3-cyclopentoxy-4-methoxyphenyl)-1-(1,1-dimethylethoxycarbonyl)pyrrolidine ($R^1$=cyclopentyl; $R^2$=H; $R^3$=—$CONH_2$; $R^4$=H; $R^5$=—$CO_2C(CH_3)_3$; $R^{12}$=methyl)

To a solution of trans-3-carboxy-4-[(3-cyclopentoxy-4-methoxy)phenyl]-1-(1,1-dimethylethoxycarbonyl)pyrrolidine (400 mg, 0.98 mmol) in 4 mL of $CH_2Cl_2$ at 0° C. was added 1,1'-carbonyldiimidazole (154 mg, 1.0 mmol). The solution was stirred for 20 min. Ammonia gas was then passed over the stirring solution for 3 min, and stirring was continued an additional 30 min. The solution was diluted with $CH_2Cl_2$ and poured into 1M $H_3PO_4$. The aqueous layer was extracted with $CH_2Cl_2$ (2×), and the combined organic layers were washed with brine, dried ($MgSO_4$), filtered, and concentrated under reduced pressure to a pale yellow foam. Silica gel chromatography (9:1, $CH_2Cl_2$:methanol) provided trans-3-aminocarbonyl-4-(3-cyclopentoxy-4-methoxyphenyl)-1-(1,1-dimethylethoxycarbonyl)pyrrolidine as a tacky white solid (275 mg, 74%). Anal. Calcd for $C_{22}H_{32}N_2O_5$: C, 65.33; H, 7.97; N, 6.93. Found: C, 65.07; H, 8.07; N, 6.85.

Example 41 trans-3-(3-Cyclopentoxy-4-methoxyphenyl)-1-(1,1-dimethylethoxycarbonyl)-4-[(N-phenylmethyl)aminocarbonyl]pyrrolidine ($R^1$=cyclopentyl; $R^2$=H; $R^3$=—$CONHCH_2$-(phenyl) $R^4$=H; $R^5$=—$CO_2C(CH_3)_3$; $R^{12}$=methyl)

To a solution of trans-3-carboxy-4-(3-cyclopentoxy-4-methoxyphenyl)-1-(1,1-dimethylethoxycarbonyl)pyrrolidine (300 mg, 0.75 mmol) in 2 mL of $CH_2Cl_2$ at 0° C. was added 1,1'-carbonyldiimidazole (120 mg, 0.75 mmol). The cooling bath was removed, and the solution was stirred at room temperature for 30 min. Benzylamine (150 mg, 1.5 mmol) was added and stirring was continued for 1 hr. The solution was diluted with ether and poured into 1M $H_3PO_4$. The aqueous layer was extracted with $CH_2Cl_2$ (2×), and the combined organic layers were washed with brine, dried ($MgSO_4$), filtered, and concentrated under reduced pressure to a pale yellow foam. Silica gel chromatography (1:1, hexanes:ethyl acetate) provided trans-3-(3-cyclopentoxy-4-methoxyphenyl)-1-(1,1-dimethylethoxycarbonyl)-4-[(N-phenylmethyl)aminocarbonyl]pyrrolidine as a tacky white solid (275 mg, 74%). Anal. Calcd for $C_{29}H_{38}N_2O_5$: C, 70.42; H, 7.74; N, 5.66. Found: C, 70.42; H, 7.80; N, 5.67.

Example 42 trans-3-[(3-Cyclopentoxy-4-methoxy)phenyl]-4-N-(1,1-dimethylethoxycarbonyl)-1-(1,1-dimethylethoxycarbonyl)pyrrolidine ($R^1$=cyclopentyl; $R^2$=H; $R^3$=—$NHCO_2C(CH_3)_3$ $R^4$=H; $R^5$=—$CO_2C(CH_3)_3$; $R^{12}$=methyl)

A solution of trans-3-carboxy-4-(3-cyclopentoxy-4-methoxyphenyl)-1-(1,1-dimethylethoxycarbonyl)pyrrolidine (1.00 g, 2.47 mmol), triethylamine (274 mg, 2.72 mmol), and diphenylphosphoryl azide (744 mg, 2.72 mmol) in 10 mL of t-butanol was heated to 90° C. for 12 hr. The resulting solution was concentrated, and the residue was partitioned between ether and 1M $H_3PO_4$. The organic layer was washed with 2N NaOH and brine, dried over $MgSO_4$, filtered, and concentrated to a colorless foam. Silica gel chromatography (5:2, hexanes:ethyl acetate) provided trans-3-[(3-cyclopentoxy-4-methoxy)phenyl]-4-N-(1,1-dimethylethoxycarbonyl)-1-(1,1-dimethylethoxycarbonyl)pyrrolidine as a white solid (658 mg, 56%): m.p. 65°–69° C. Anal. Calcd for $C_{26}H_{40}N_2O_6$: C, 65.52; H, 8.46; N, 5.88. Found: 0, 65.34; H, 8.43; N, 5.98.

The following compounds were prepared according to the general procedure set forth above in Example 42:

Example 43 trans-3-(3-cyclopentoxy-4-methoxyphenyl)-4-N-(1,1-dimethylethoxycarbonyl)-1-(methoxycarbonyl)pyrrolidine:

($R^1$=cyclopentyl; $R^2$=H; $R^3$=—$NHCO_2C(CH_3)_3$; $R^4$=H; $R^5$=—$CO_2CH_3$; $R^{12}$=methyl)
35%; Anal. Calcd for $C_{23}H_{34}N_2O_6$: C, 63.58; H, 7.89; N, 6.45. Found: C, 63.35; H, 7.91; N, 6.40.

Example 44 trans-3-(3-cyclopentoxy-4-methoxyphenyl)-4-N-(1,1-dimethylethoxycarbonyl)-1-(phenylmethoxycarbonyl)pyrrolidine:

($R^1$=cyclopentyl; $R^2$=H; $R^3$=—$NHCO_2C(CH_3)_3$; $R^4$=H; $R^5$=—$CO_2CH_2$-phenyl; $R^{12}$=methyl)
41%; Anal. Calcd for $C_{29}H_{38}N_2O_6$: C, 68.21; H, 7.50; N, 5.49. Found: C, 67.96; H, 7.44; N, 5.63.

Example 45 trans-3-[(3-Cyclopentoxy-4-methoxy)phenyl]-4-[N-(1,1-dimethylethoxycarbonyl)-N-methyl]-1-(phenylmethoxycarbonyl)pyrrolidine ($R^1$=cyclopentyl; $R^2$=H; $R^3$=—$N(CH_3)CO_2C(CH_3)_3$; $R^4$=H; $R^5$=—$CO_{CH2}$-phenyl; $R^{12}$=methyl)

To a solution of trans-3-(3-cyclopentoxy-4-methoxyphenyl)-4-N-(1,1-dimethylethoxycarbonyl)-1-(phenylmethoxycarbonyl)pyrrolidine (200 mg, 0.39 mmol) in 3 mL of DMF was added sodium bis(trimethylsilyl)amide (0.43 mL, 0.43 mmol). After 5 min methyl iodide (111 mg, 0.78 mmol) was added. The reaction mixture was stirred until TLC analysis indicated complete reaction. The reaction was diluted with ether and washed with 1M $H_3PO_4$ and brine. The organic layer was dried over $MgSO_4$, filtered, and concentrated under reduced pressure. Silica gel chromatography (2:1, hexanes:ethyl acetate), performed twice, provided trans-3-(3-cyclopentoxy-4-methoxyphenyl)-4-[N-(1,1-dimethylethoxycarbonyl)-N-methyl]-1-(phenylmethoxycarbonyl)pyrrolidine as a white solid (110 mg, 54%), m.p. 44°–47° C. Anal. Calcd for $C_{30}H_{40}N_2O_6$: C, 68.68; H, 7.68; N, 5.34. Found: C, 68.55; H, 7.69; N, 5.35.

Example 46 trans-3-(3-Cyclopentoxy-4-methoxyphenyl)-4-N-(methylsulfonyl)-1-(phenylmethoxycarbonyl)pyrrolidine ($R^1$=cyclopentyl; $R^2$=H; $R^3$=—$NHSO_2CH_3$; $R^4$=H; $R^5$=—$CO_2CH_2$-phenyl; $R^{12}$=methyl)

To a solution of trans-3-(3-cyclopentoxy-4-methoxyphenyl)-4-N-(1,1-dimethylethoxycarbonyl)-1-(phenylmethoxycarbonyl)pyrrolidine (130 mg, 0.26 mmol) in 0.5 mL of $CH_2Cl_2$ was added 0.5 mL of trifluoroacetic acid. When the reaction was judged complete by TLC analysis, the reaction was diluted with $CH_2Cl_2$ and treated with 2N NaOH. The organic layer was dried over $K_2CO_3$, filtered, and concentrated under reduced pressure to an oil. This oil was dissolved in 1 mL of $CH_2Cl_2$ and treated with triethylamine (103 mg, 1.01 mmol), followed by methanesulfonyl chloride (40 mg, 0.31 mmol). The solution was stirred for 12 hr, diluted with ethyl acetate, washed with 1M $H_3PO_4$, dried over $MgSO_4$, filtered, and concentrated under reduced pressure. Silica gel chromatography (9:1, $CH_2Cl_2$:ethyl acetate) provided trans-3-(3-cyclopentoxy-4-methoxyphenyl)-4-N-(methylsulfonyl)-1-(phenylmethoxycarbonyl)pyrrolidine as a foamy white solid (98 mg, 79%). Anal. Calcd for $C_{25}H_{32}N_2O_6S$: C, 61.46; H, 6.60; N, 5.73. Found: C, 61.56; H, 6.68; N, 5.78.

Example 47 trans-3-(3-Cyclopentoxy-4-methoxyphenyl)-1-(phenylmethoxycarbonyl)-4-N-(trifluoromethylsulfonyl)pyrrolidine ($R^1$=cyclopentyl; $R^2$=H; $R^3$=—$NHSO_2CF_3$; $R^4$=H; $R^5$=—$CO_2CH_2$-phenyl; $R^{12}$=methyl)

To a solution of trans-3-[(3-cyclopentoxy-4-methoxy)phenyl]-4-N-(1,1-dimethylethoxycarbonyl)-1-(phenylmethoxycarbonyl)pyrrolidine (201 mg, 0.39 mmol) in 0.5 mL of $CH_2Cl_2$ at 0° C. was added 1.5 mL of trifluoroacetic acid. When the reaction was judged complete by TLC analysis, the reaction was diluted with $CH_2Cl_2$ and treated with 2N NaOH. The organic layer was dried over $K_2CO_3$, filtered, and concentrated under reduced pressure to an oil. This oil was dissolved in 1.5 mL of $CH_2Cl_2$ and treated with triethylamine (159 mg, 1.58 mmol), followed by trifluoromethanesulfonic anhydride (134 mg, 0.47 mmol). The solution was stirred for 4 hr, diluted with ethyl acetate, washed successively with 1M $H_3PO_4$, sat $NaHCO_3$, and brine. The organic layer was dried over $MgSO_4$, filtered, and concentrated under reduced pressure. Silica gel chromatography (3:1:1, hexanes:$CH_2Cl_2$:ethyl acetate) provided trans-3-(3-cyclopentoxy-4-methoxyphenyl)-1-(phenylmethoxycarbonyl)-4-N-(trifluoromethylsulfonyl) pyrrolidine as a foamy white solid (75 mg, 35%). Anal. Calcd for $C_{25}H_{29}F_3N_2O_6S$: C, 55.34; H, 5.39; N, 5.16. Found: C, 55.31; H, 5.71; N, 4.74.

Example 48 trans-3-(3-Cyclopentoxy-4-methoxyphenyl)-4-N-(phenylsulfonyl)-1-(phenylmethoxycarbonyl) pyrrolidine ($R^1$=cyclopentyl; $R^2$=H; $R^3$=—$NHSO_2$-phenyl; $R^4$=H; $R^5$=—$CO_2CH_2$-phenyl; $R^{12}$=methyl)

To a solution of trans-3-(3-cyclopentoxy-4-methoxyphenyl)-4-N-(1,1-dimethylethoxycarbonyl)-1-(phenylmethoxycarbonyl)pyrrolidine (130 mg, 0.26 mmol) in 0.5 mL of $CH_2Cl_2$ was added 0.5 mL of trifluoroacetic acid. When the reaction was judged complete by TLC analysis, the reaction was diluted with $CH_2Cl_2$ and treated with 2N NaOH. The organic layer was dried over $K_2CO_3$, filtered, and concentrated under reduced pressure to an oil. This oil was dissolved in 1 mL of $CH_2Cl_2$ and treated with triethylamine (103 mg, 1.01 mmol), followed by phenylsulfonyl chloride (54 mg, 0.31 mmol). The solution was stirred for 12 hr, diluted with ethyl acetate, washed with 1M $H_3PO_4$, dried over $MgSO_4$, filtered, and concentrated under reduced pressure. Silica gel chromatography (9:1, $CH_2Cl_2$:ethyl acetate) provided trans-3-(3-cyclopentoxy-4-methoxyphenyl)-4-N-(methylsulfonyl)-1-(phenylmethoxycarbonyl)pyrrolidine as a foamy white solid (121 mg, 86%). Anal. Calcd for $C_{30}H_{34}N_2O_6S$: C, 65.43; H, 6.22; N, 5.09. Found: C, 65.57; H, 6.30; N, 5.04.

Example 49 trans-3-(3-Cyclopentoxy-4-methoxyphenyl)-1-methoxycarbonyl-4-N-(methoxycarbonyl)pyrrolidine ($R^1$=cyclopentyl; $R^2$=H; $R^3$=—$NHCO_2CH_3$; $R^4$=H; $R^5$=—$CO_2CH_3$; $R^{12}$=methyl)

To a solution of trans-3-(3-cyclopentoxy-4-methoxyphenyl)-4-N-(1,1-dimethylethoxycarbonyl)-1-(1,1-dimethylethoxycarbonyl)pyrrolidine (200 mg, 0.42 mmol) in 0.5 mL of $CH_2Cl_2$ was added 1.5 mL of trifluoroacetic acid. When the reaction was judged complete by TLC analysis, the reaction was diluted with $CH_2Cl_2$ and treated with 2N NaOH. The organic layer was dried over $K_2CO_3$, filtered, and concentrated under reduced pressure to an oil. This oil was dissolved in 3 mL of $CH_2Cl_2$, cooled to 0° C. and treated with DMAP (112 mg, 0.92 mmol), followed by methyl chloroformate (217 mg, 2.31 mmol). The solution was stirred for 2 hr, diluted with ethyl acetate, washed with 1M $H_3PO_4$, dried over $MgSO_4$, filtered, and concentrated under reduced pressure. Silica gel chromatography (9:1, $CH_2Cl_2$:ethyl acetate) provided trans-3-(3-cyclopentoxy-4-methoxyphenyl)-1-methoxycarbonyl-4-N-(methoxycarbonyl)pyrrolidine as a foamy white solid (100 mg). Anal. Calcd for $C_{20}H_{28}N_2O_6$•0.25 $H_2O$: C, 60.52; H, 7.24; N, 7.06. Found: C, 60.37; H, 7.28; N, 6.97.

Example 50 trans-1-Aminocarbonyl-3-(3-cyclopentoxy-4-methoxyphenyl)-4-N-(1,1-dimethylethoxycarbonyl) pyrrolidine ($R^1$=cyclopentyl; $R^2$=H; $R^3$=—$NHCO_2C(CH_3)_3$; $R^4$=H; $R^5$=—$CONH_2$; $R^{12}$=methyl)

To a solution of trans-3-(3-cyclopentoxy-4-methoxyphenyl)-4-N-(1,1-dimethylethoxycarbonyl)-1-(phenylmethoxycarbonyl)pyrrolidine (116 mg, 0.23 mmol) in 3 mL of 4% $HCO_2H$:methanol was added 10% Pd-C (13 mg). A balloon of $H_2$ gas was then attached and the reaction suspension was stirred at room temperature under an atmosphere of $H_2$. When the reaction was judged complete by TLC analysis, the reaction was diluted with methanol and filtered through a plug of Celite. Concentation under reduced pressure led to an off-white solid, which was partitioned between $CH_2Cl_2$ and sat. $NaHCO_3$. The organic layer was dried over $K_2CO_3$, filtered and concentrated under reduced pressure. The resulting product was dissolved in 1 mL of $CH_2Cl_2$ and treated at 0° C. with DMAP (85 mg) and trimethylsilyl isocyanate (280 mg). The solution was stirred for 72 hr, diluted with $CH_2Cl_2$, washed successively with 1M $H_3PO_4$, sat $NaHCO_3$, and brine. The organic layer was dried over $K_2CO_3$, filtered, and concentrated under reduced pressure. Silica gel chromatography (9:1, $CH_2Cl_2$:methanol) provided trans-1-aminocarbonyl-3-(3-cyclopentoxy-4-methoxyphenyl)-4-N-(1,1-dimethylethoxycarbonyl) pyrrolidine as a white solid (57 mg, 60%). Anal. Calcd for $C_{22}H_{33}N_3O_5$: C, 62.99; H, 7.93; N, 10.02. Found: C, 62.81; H, 7.95; N, 9.97.

Example 51 trans-1-Aminothiocarbonyl-3-(3-Cyclopentoxy-4-methoxyphenyl)-4-(methoxycarbonyl)pyrrolidine ($R^1$=cyclopentyl; $R^2$=H; $R^3$=—$CO_2CH_3$; $R^4$=H; $R^5$=—$CSNH_2$; $R^{12}$=methyl)

To a solution of trans-3-(3-cyclopentoxy-4-methoxyphenyl)-4-(methoxycarbonyl)pyrrolidine (250 mg, 0.78 mmol) in 2 mL of $CH_2Cl_2$ at 0° C. was added DMAP (286 mg, 2.34 mmol), followed by trimethylsilyl isothiocyanate (1.09 mL, 7.8 mmol). The solution was stirred for 72 hr, diluted with $CH_2Cl_2$, and washed with 1M $H_3PO_4$. The aqueous layer was extracted with $CH_2Cl_2$ (2×). The combined organic layers were dried over $MgSO_4$, filtered and concentrated to a colorless oil. Silica gel chromatography (9:1, $CH_2Cl_2$:methanol), followed again by silica gel chromatography (1:1, hexanes:ethyl acetate) provided trans-1-aminothiacarbonyl-3-(3-cyclopentoxy-4-methoxyphenyl)-4-(methoxycarbonyl)pyrrolidine as a foamy white solid (215 mg, 73%). Anal. Calcd for $C_{19}H_{26}N_2O_4S$: C, 60.29; H, 6.92; N, 7.40. Found: C, 60.31; H, 6.95; N, 7.34.

Example 52 trans-1-Cyano-3-(3-cyclopentoxy-4-methoxyphenyl)-4-(methoxycarbonyl)pyrrolidine ($R^1$=cyclopentyl; $R^2$=H; $R^3$=—$CO_2CH_3$; $R^4$=H; $R^5$=—CN; $R^{12}$=methyl To a solution of trans-3-(3-cyclopentoxy-4-methoxyphenyl)-4-(methoxycarbonyl)pyrrolidine (300 mg, 0.94 mmol) and $K_2CO_3$ (195 mg, 1.5 mmol) in 5 mL of $CH_3CN$ at 0° C. was added cyanogen bromide (120 mg, 1.13 mmol). The solution was stirred for 24 hr, diluted with $H_2O$ and ethyl acetate, and washed with brine. The combined organic layers were dried over $MgSO_4$, filtered and concentrated to an oil. Silica gel chromatography (3:1, hexanes:ethyl acetate) provided trans-1-cyano-3-(3-cyclopentoxy-4-methoxyphenyl)-4-(methoxycarbonyl)pyrrolidine as a white solid (166 mg, 51%).m.p. 78°–80° C. Anal. Calcd for $C_{19}H_{24}N_2O_4$: C, 66.26; H, 7.02; N, 8.13. Found: C, 66.30; H, 7.04; N, 8.15.

Example 53 trans-3-(3-Cyclopentoxy-4-methoxyphenyl)-4-methoxycarbonyl-1-(phenylmethoxycarbonyl) pyrrolidine ($R^1$=cyclopentyl; $R^2$=H; $R^3$=—$CO_2CH_3$; $R^4$=H; $R^5$=—$CO_2CH_2$-phenyl; $R^{12}$=methyl)

trans-3-(3-Cyclopentoxy-4-methoxyphenyl)-4-methoxycarbonyl-1-(phenylmethyl)pyrrolidine (3.1 g, 7.5 mmol) was dissolved in 50 mL of 4% $HCO_2H$:methanol. While stirring at room temperature, 10% Pd/C (400 mg) was added in small portions. After 16 hrs the reaction was diluted with methanol. Filtration through Celite followed by concentration under reduced pressure yielded a yellow oil residue. This residue was dissolved in $CH_2Cl_2$ and DMAP (1.19 g, 9.75 mmol) and benzyl chloroformate (1.5 g, 8.2 mmol) were added. The resulting solution was stirred at room temperature. When reaction was judged complete by TLC analysis the mixture was partitioned between $CH_2Cl_2$ and 1M $H_3PO_4$. The layers were separated and the aqueous layer was extracted with $CH_2Cl_2$ (2×). The organic layers were combined, dried ($MgSO_4$), filtered, and concentrated under reduced pressure to afford a pale oil. Chromatography on silica gel (3:2, hexanes:ethyl acetate) provided trans-3-(3-cyclopentoxy-4-methoxyphenyl)-4-methoxycarbonyl-1-(phenylmethoxycarbonyl)pyrrolidine as a white solid (1.34 g, 40%). m.p. 85° C. Anal. Calcd for $C_{26}H_{31}NO_6$: C, 68.86; H, 6.89; N, 3.09. Found: C, 68.81; H, 6.94; N, 2.99.

Example 54 trans-3-(3-Cyclopentoxy-4-methoxyphenyl)-4-methoxycarbonyl-1-(methylethoxycarbonyl) pyrrolidine ($R^1$=cyclopentyl; $R^2$=H; $R^3$=—$CO_2CH_3$; $R^4$=H; $R^5$=—$CO_2CH(CH_3)_2$; $R^{12}$=methyl)

To a solution of trans-3-(3-cyclopentoxy-4-methoxyphenyl)-4-(methoxycarbonyl)pyrrolidine (500 mg, 1.57 mmol) in 4 mL of $CH_2Cl_2$ was added at 0° C. 4-dimethylaminopyridine (250 mg, 2.04 mmol), followed by isopropyl chloroformate (1.7 mL of a 1M toluene solution). After 16 hr the reaction was diluted with $CH_2Cl_2$ and washed with 1M $H_3PO_4$. The organic layer was dried over $MgSO_4$, filtered, and concentrated under reduced pressure. Silica gel chromatography (2:1, hexanes:ethyl acetate) provided trans-3-(3-cyclopentoxy-4-methoxyphenyl)-4-methoxycarbonyl-1-(methylethoxycarbonyl)pyrrolidine as a white solid (280 mg, 44%). Anal. Calcd for $C_{22}H_{29}NO_6$: C, 65.17; H, 7.71; N, 3.45. Found: C, 65.16; H, 7.69; N, 3.43.

Example 55

3-(3-Cyclopentoxy-4-methoxyphenyl)-1-(1,1-dimethylethoxycarbonyl)-4-methoxycarbonyl-4-methylpyrrolidine ($R^1$=cyclopentyl; $R^2$=H; $R^3$=—$CO_2CH_2CH_3$; $R^4$=$CH_3$; $R^5$=—$CO_2C(CH_3)_3$; $R^{12}$=methyl)

To a solution of trans-3-(3-cyclopentoxy-4-methoxyphenyl)-4-methoxycarbonyl-4-methylpyrrolidine (317 mg, 0.90 mmol) in 1.5 mL of $CH_2Cl_2$ at 0° C. was added 4-dimethylaminopyridine (145 mg, 1.17 mmol), followed by di-t-butyl dicarbonate (259 mg, 1.17 mmol). After 12 hr the reaction was diluted with ether and washed with 1M $H_3PO_4$. The organic layer was dried over $MgSO_4$, filtered, and concentrated under reduced pressure. Silica gel chromatography (5:2, hexanes:ethyl acetate) provided trans-3-(3-cyclopentoxy-4-methoxyphenyl)-1-(1,1-dimethylethoxycarbonyl)-4-ethoxycarbonyl-4-methylpyrrolidine as a viscous oil (358 mg, 87%). Anal. Calcd for $C_{25}H_{37}NO_6$: C, 67.09; H, 8.33; N, 3.13. Found: C, 66.95; H, 8.36; N, 3.06.

Example 56 trans-3-(3-Cyclopentoxy-4-methoxyphenyl)-1-methoxycarbonyl-4-(methoxymethyl)pyrrolidine ($R^1$=cyclopentyl; $R^2$=H; $R^3$=—$CH_2OCH_3$; $R^4$=H; $R^5$=—$CO_2CH_3$; $R^{12}$=methyl)

To a solution of trans-3-(-cyclopentoxy-4-methoxyphenyl)-4-hydroxymethyl-1-(methoxycarbonyl) pyrrolidine (250 mg, 0.72 mmol) and methyl iodide (3.60 mmol, 0.22 mL) in 1.5 mL of THF was added sodium hydride (86.4 mg of 60% oil dispersion, 2.16 mmol). After 10 min an additional 0.22 mL of methyl iodide and 58 mg of sodium hydride were added. After 15 min $H_2O$ was added dropwise until bubbling ceased. The mixture was diluted with $CH_2Cl_2$ and washed with $H_2O$. The aqueous layer was extracted with $CH_2Cl_2$ (3×). The organic layers were dried ($K_2CO_3$), filtered and concentrated under reduced pressure to an oil. Silica gel chromatography (2:1, hexanes:ethyl acetate) provided trans-3-(3-cyclopentoxy-4-methoxyphenyl)-1-methoxycarbonyl-4-(methoxymethyl) pyrrolidine as a colorless oil (234 mg, 89%). $^1$H-NMR (300 MHz): δ 3.29 (s, 3), 3.72 (s, 3), 3.83 (s, 3).

Compounds of Formula (I) which contain acidic moieties may form pharmaceutically acceptable salts with suitable cations. Suitable pharmaceutically acceptable cations include alkali metal (e.g., sodium or potassium) and alkaline earth metal (e.g., calcium or magnesium) cations. In light of the foregoing, any reference to compounds of the present invention appearing herein is intended to include both compounds of Formula (I) as well as pharmaceutically acceptable salts and solvates thereof.

As previously mentioned, the compounds of the present invention are useful for inhibiting PDE-IV activity in a mammal. For example, PDE-IV inhibitors are useful in the treatment of a variety of allergic, autoimmune and inflammatory diseases. Inflammation is a localized, protective response elicited by injury or destruction of tissues, which serves to destroy, dilute or wall off (sequester) both the injurious agent and the injured tissue (see Dorland's Medical Dictionary). The term "inflammatory disease", as set forth herein, is intended to mean any disease in which an excessive or unregulated inflammatory response leads to excessive inflammatory symptoms, host tissue damage or loss of tissue function. Additionally, the term "autoimmune disease", as set forth herein, is intended to mean any group of disorders in which tissue injury is associated with humoral or cell-mediated responses to the body's own constutuents (Id.). The term "allergic disease" is intended to mean any symptoms, tissue damage or loss of tissue function resulting from allergy (a hypersensitive state of the immune system brought about by exposure to a particular substance which biochemically interacts with an organism resulting in a change in the organism's capacity to immunologically react with the substance) (Id.). The term "arthritic disease" is intended to mean any of a large family of diseases all of which are characterized by inflammatory lesions of the joints attributable to a variety of etiologies. The term "dermatitis" is intended to mean any of a large family of diseases of the skin which are characterized by inflammation of the skin attributable to a variety of etiologies (Id.). The term "transplant rejection", as set forth herein, is intended to mean any immune reaction directed against grafted tissue [including organ and cell (e.g., bone marrow)] and characterized by a loss of function of the grafted and surrounding tissues, pain, swelling, leukocyteisis and thrombocytopenia (Id.).

The present invention also provides a method for modulating cAMP levels in a mammal as well as a method for treating diseases characterized by elevated cytokine levels.

The term "cytokine", as set forth herein, is intended to mean any secreted polypeptide that affects the functions of other cells, and is a molecule which modulates interactions between cells in the immune or inflammatory response. A cytokine includes, but is not limited to monokines and lymphokines regardless of which cells produce them. For instance, a monokine is generally referred to as being produced and secreted by a monocyte however many other cells produce monokines, such as natural killer cells, fibreblasts, basophils, neutrophils, endothelial cells, brain astrocytes, bone marrow stromal cells, epidermal keratinocytes, and B-lymphocytes. Lymphokines are generally referred to as being produced by lymphocyte cells. Examples of cytokines for the present invention include, but are not limited to Interleukin-1 (IL-1), Interleukin-6 (IL-6), Tumor Necrosis Factor-alpha (TNFα) and Tumor Necrosis Factor beta (TNFβ).

Additionally, the present invention provides a method for reducing TNF levels in a mammal which comprises administering an effective amount of a compound of Formula (I). The term "reducing TNF levels", as set forth herein, is intended to mean either:

a) decreasing excessive in vive TNF levels in a mammal to normal levels or below normal levels by inhibition of the in vivo release of TNF by all cells, including but not limited to monocytes or macrophages; or b) inducing a down regulation, at the translational or transcription level, of excessive in vive TNF levels in a mammal to normal levels or below normal levels; or c) inducing a down regulation, by inhibition of the direct synthesis of TNF as a postranslational event.

Moreover, the compounds of the present invention are useful in suppressing inflammatory cell activation. The term "inflammatory cell activation", as set forth herein, is intended to mean the induction by a stimulus (including but not limited to cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including but not limited to major histocompatability antigens or cell adhesion molecules) in inflammatory cells (including but not limited to monocytes, macrophages, T lymphocytes, B lymphocytes, granulocytes, polymorphonuclear leukocytes, mast cells, basophils, eosinophils and endothelial cells). It will be appreciated by those schooled in the art that the activation of one or a combination of these phenotypes in these cells can contribute to the initiation, perpetuation or exacerbation of an inflammatory condition.

Furthermore, the compounds of the present invention are useful in causing airway smooth muscle relaxation (see Giebycz and Barnes, Biochem Pharmacol 42:663, 1991), bronchodilation (see Heaslip et al, J Pharmac exp Ther 257:741, 1991) and prevention of bronchoconstriction (see Small, et al, Eur J Pharmacol 192:417, 1991; Giebycz and Barnes, Biochem Pharmacol 42:663, 1991).

Some examples of diseases for which the compounds of the present invention are useful in treating include arthritic diseases such as rheumatoid arthritis, osteoarthritis, gouty arthritis and spondylitis. Examples of other such diseases include sepsis, septic shock, endotoxic shock, gram negative sepsis, gram positive sepsis, toxic shock syndrome, asthma, chronic bronchitis, allergic rhinitis, allergic conjunctivitis, vernal conjunctivitis, eosinophilic granuloma, adult respiratory distress syndrome, chronic pulmonary inflammatory disease, silicosis, pulmonary sarcoidosis, reperfusion injury of the myocardium, brain or extremities, fibrosis including cystic fibrosis, keloid formation, scar formation, atherosclerosis, autoimmune diseases such as lupus erythematosus and transplant rejection disorders (e.g. graft vs. host reaction and allograft rejection), chronic granulonephritis, inflammatory bowel diseases such as Crohn's disease and ulcerative colitis and inflammatory dermatoses such as atopic dermatitis, psoriasis or urticaria.

Other examples of such diseases or related conditions include pyrexia, cachexia, cachexia secondary to infection or malignancy, cachexia secondary to acquired immune deficiency syndrome (AIDS), ARC (AIDS related complex), AIDS, cerebral malaria, osteoporosis and bone resorption diseases, keloid formation, scar tissue formation and fever and myalgias due to infection. In addition, the compounds of the present invention are useful in the treatment of diabetes insipidus and central nervous system disorders, such as depression and multi-infarct dementia.

The present invention also provides for novel pharmaceutical compositions of the compounds of Formula (I). While it is possible that compounds of the present invention may be therapeutically administered as the raw chemical, it is preferable to present the active ingredient as a pharmaceutical formulation. Accordingly, the present invention further provides for pharmaceutical formulations comprising a compound of Formula (I) or a pharmaceutically acceptable salt thereof together with one or more pharmaceutically acceptable carriers and, optionally, other therapeutic and/or prophylactic ingredients. The carrier(s) must be "acceptable" in the sense of being compatible with the other ingredients of the formulation and not deleterious to the recipient thereof.

It will be appreciated by those skilled in the art that reference herein to treatment extends to prophylaxis as well as the treatment of established diseases or symptoms. It will further be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.001 mg/kg to about 100 mg/kg per day. The desired dose may conveniently be presented in a single dose or as divided doses administered at appropriate intervals, for example as two, three, four or more sub-doses per day.

Formulations of the present invention may be administered in standard manner for the treatment of the indicated diseases, such as orally, parenterally, sublingually, transdermally, rectally, via inhalation or via buccal administration. For buccal administration, the composition may take the form of tablets or lozenges formulated in conventional manner. For example, tablets and capsules for oral administration may contain conventional excipients such as binding agents, (for example, syrup, accacia, gelatin, sorbitol, tragacanth, mucilage of starch or polyvinylpyrrolidone), fillers (for example, lactose, sugar, microcrystalline.cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulphate. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid.

Such preparations may also be formulated as suppositories, e.g., containing conventional suppository bases such as cocoa butter or other glycerides. Compositions for inhalation can be typically provided in the form of a solution, suspension or emulsion that may be administered as a dry powder or in the form of an aerosol using a conventional propellant such as dichlorodifluoromethane or trichlorofluoromethane. Typical transdermal formulations comprise a conventional aqueous or non-aqueous vehicles, such as creams, ointments, lotions or pastes or are in the form of a medicated plaster, patch or membrane.

Additionally, compositions the present invention may be formulated for parenteral administration by injection or continuous infusion. Formulations for injection may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle (e.g., sterile, pyrogen-free water) before use.

The composition according to the invention may also be formulated as a depot preparation. Such long acting formulations may be administered by implantation (for example, subcutaneously or intramuscularly) or by intramuscular injection. Accordingly, the compounds of the invention may be formulated with suitable polymeric or hydrophobic materials (as an emulsion in an acceptable oil, for example), ion exchange resins or as sparingly soluble derivatives as a sparingly soluble salt, for example.

The biological activity of the compounds of Formula (I) was evaluated according to the following protocols with appropriate data provided below.

EXPERIMENTAL

Cloning and expression of human recombinant PDE-IV

In order to obtain large quantities of cyclic AMP-specific Type IV phosphodiesterase (PDE-IV) protein to screen inhibitors, the cloning and expression of a human PDE-IV (hPDE-IV) from myelocytic lineage cells was performed. Previous PDE activity data has shown that dibutyryl cyclic AMP (dbcAMP)-differentiated HL-60 cells (ATCC,CCL 240; Verghese, M. unpublished results). Therefore, a cDNA library constructed from dbcAMP-treated HL 60 mRNA was screened to isolate a PDE-IV clone.

A lambda gt10 dibutyryl cAMP-stimulated HL-60 cDNA library (obtained from Dr. R. Snyderman, Duke University Medical Center) was screened first by the polymerase chain reaction (PCR) technique (see "PCR Protocols, A guide to Methods and Application" Eds. Innis, M. A. et al., Academic Press Inc. (1990) with rat PDE-IV primers in order to obtain partial hPDE-IV sequence. Three sets of sense and antisense primers were made to the conserved region of PDE-IV from rat (Colicelli, J., et al., PNAS 86:3599 (1989), Swinnen, J. V., et al., PNAS 86:5325 (1989)). The primers were used in various combinations to amplify a set of PCR fragments and show that the library contained PDE-IV inserts. The resulting PCR fragments were subcloned and sequenced (Sanger, F., et al., PNAS 74:5463 (1977) and found to contain extensive homology with the kPDE-IV sequence from rat. Two of the primers from the primer sets that were found to have 100% homology with sequence from the PCR fragments were used to screen the cDNA library.

Two cDNA clones, hPDE-R and PDE-M, were obtained by conventional hybridization screening (in "Molecular Cloning, A Laboratory Manual" Volume 2, Eds. Sambrook, J., et al., Cold Spring Harbor Laboratory Press (1989)) of the HL-60 cDNA library. The eDNA inserts of hPDE-M and hPDE-R were subcloned into M13mp18a (Messing J., Methods of Enzymology, 101:20 (1983)) and sequenced. Sequence analysis showed regions of perfect homology between hPDE-M and hPDE-R with divergent sequences at both the 5' and 3' ends (see FIG. 1). These cDNAs also had regions of extensive homology with the rat PDE-IV. Analysis of all the sequence information from both clones hPDE-R and hPDE-M resulted in the identification of an open reading frame of 1462 bases which should code for a protein of approximately 55 kD.

In particular, FIG. 1 sets forth the EcoRI eDNA inserts from the Lambda gt10 cDNA library, identified as hPDE-M and hPDE-R. These were subcloned into M13, generating the constructs M13mp18a PDE-M and M13mp18a PDE-R, and sequenced. Sequence analysis found regions of perfect homology between hPDE-M and hPDE-R (hatched box) with divergent sequences at both the 5' and 3' ends. Clone hPDE-R started internally in the coding region, diverged from PDE-M (open box), contained a stop codon (TAA), and ended with a 3' untranslated region (thin bar). Clone PDE-M began with an intron, contained an internal intron (loop), as well as a 3' region that diverged from PDE-R and is a potential intron (bold box and bar). PDE-M also contained a continuation of the coding sequence (checkered box). An in-frame methionine codon (ATG) was located that had stop codons in all three reading frames, 5' to this methionine.

Figure 2:
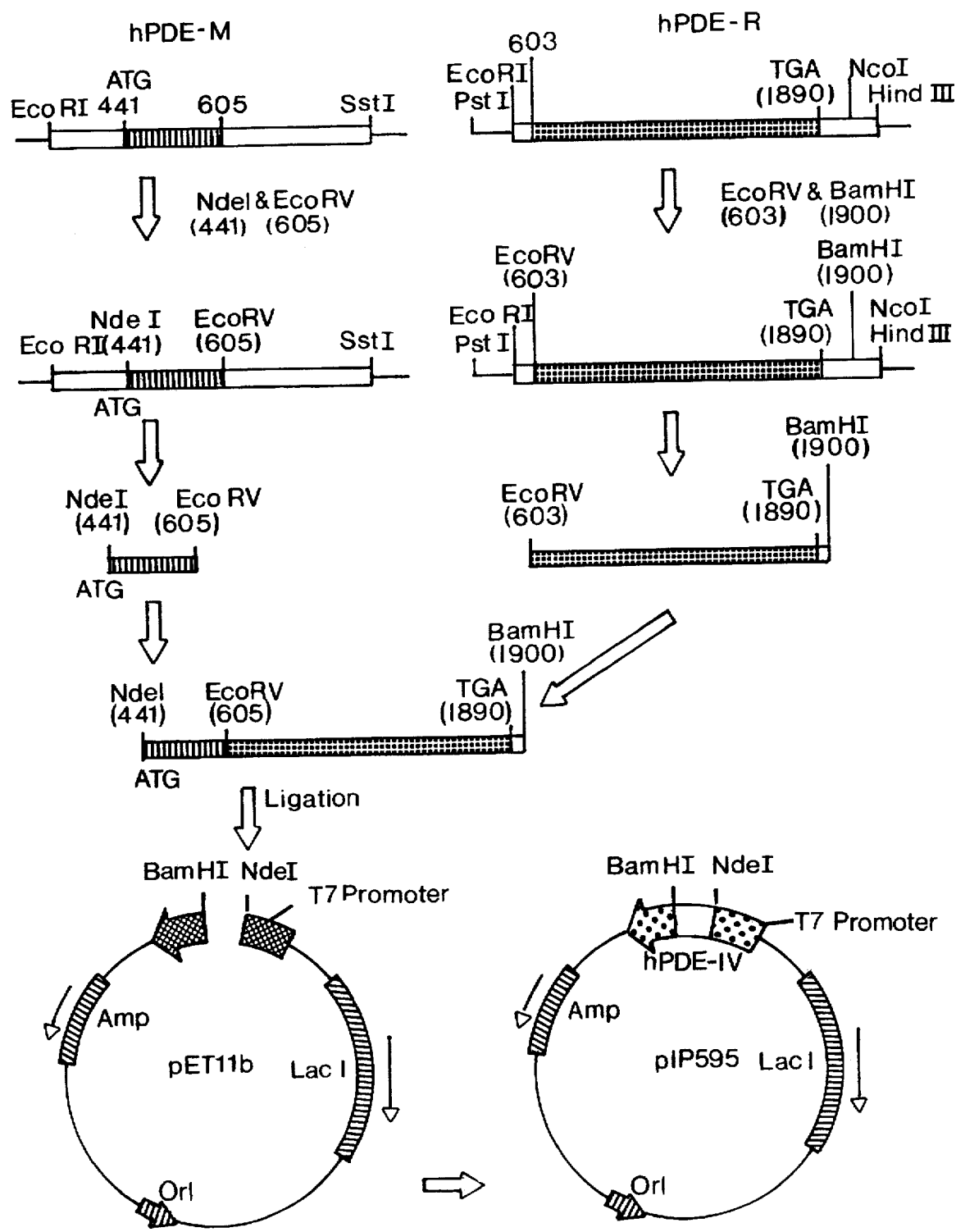
FIG. 2 sets forth the site directed mutagenesis and assembly of PDE-IV E. coli expression construction.

To express this PDE-IV in E. coil, hPDE-M and hPDE-R were modified by site directed mutagenesis in order to join sequences from the 5' region of hPDE-M to the 3' region of hPDE-R (see FIG. 2). The restriction fragments were ligated into the pET vector expression system (obtained from Novagen Inc.) which places a coding region under the control of the bacteriophage T7 promoter. The resulting clone, pIP595, and intermediates were characterized by sequence analysis during mutagenesis and assembly. The plasmid, pIP595, yielded a high level of an approximately 55 kD protein, denoted herein as GRI-PDE-IV, which was purified, sequenced and characterized in order to verify that it was an active PDE-IV.

In particular, FIG. 2 illustrates how hPDE-IV was generated by modifying hPDE-M and hPDE-R by site-directed mutagenesis to add restriction sites to assemble hPDE-IV. hPDE-M was modified by adding an NdeI site at the start codon(ATG 441) and an EcoRV site at by 605,5' to the internal intron (see FIG. 1). hPDE-R was modified by adding an EcoRV site at bp 603 and a BamHI site directly 3' to the stop codon at position 1900 bp, 3' of the stop codon (TGA 1890). The EcoRV site was chosen at this position because it could be introduced without altering any amino acids in the translated peptide. The NdeI to EcoRV fragment from hPDE-M and the EcoRV to BamHI fragment from hPDE-R were purified and ligated into the pET vector plasmid pET11 b digested with NdeI and BamHI to produce a functional expression construct, pIP595, of hPDE-IV. This construct was used to express hPDE-IV in *E. coli*. The additional restriction sites EcoRI, SstI, PstI, NcoI, and HindIII, are included. The Amp resistance gene (Amp), the Lac I gene (Lac I), the orgin of replication (ori) and the T7 transcription unit (T7 pro and stippled arrow on plasmid) for pET11 b are also shown.

The GRI-PDE-IV protein was also placed into a baculovirus expression system. Site directed mutagenesis was used to make a similar construct as in pIP595 in the vector pJP10Z (Vialard, J., Journal of Virology 64:37 (1990)) used for baculovirus expression (see FIG. 3). This vector places a coding region under the control of the polyhedron promoter for constitutive high levels of expression. The resulting clone, pIP596, and intermediates were also characterized by sequence analysis during mutagenesis and assembly. A recombinant baculovirus was obtained after co-transfection of the pIP596 construct with wild type virus. This recombinant virus was used to express large amounts of this protein in SF9 insect cells.

Figure 3:
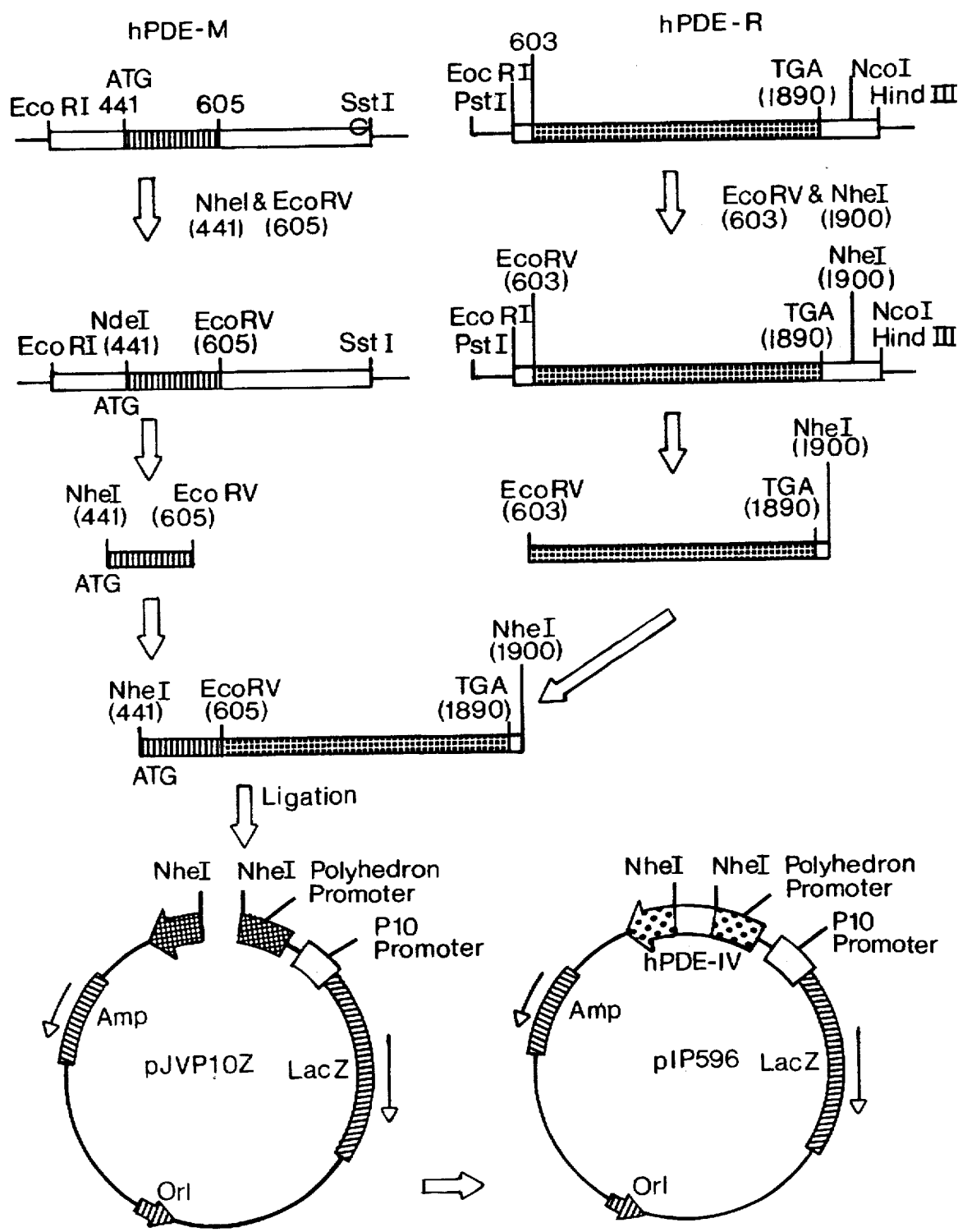
FIG. 3 sets forth the site directed mutagenesis and assembly of PDE-IV baculovirus expression construction.

In particular, FIG. 3 illustrates how hPDE-IV was generated by modifying hPDE-M and hPDE-R as in FIG. 2 by site-directed mutagenesis to add restriction sites to assemble hPDE-IV for baculovirus expression. hPDE-M was modified by adding an NheI site at the start codon and an EcoRV site at bp 605, 5' to the internal intron. hPDE-R was modified by adding an EcoRV site at bp 603 and a NheI site directly 3' to the stop codon. The NheI to EcoRV fragment from hPDE-M and the EcoRV to NheI fragment from hPDE-R were ligated into the baculovirus vector plasmid pJVP10Z digested with NheI to produce the construct pIP596 of hPDE-IC. This construct was used to co-transfect SF9 insect cells along with wild type baculovirus to generate recombinant virus for expression human recombinant PDE-IV (hrPDE-IV). The additional restriction sites EcoRI, SstI, PstI, NcoI, and HindIII, are included. The Amp resistance gene (AMP), the P10 promoter and the Lac Z gene (P10 Promoter, Lac Z), the origin of replication (ori), and the Polyhedron transcription unit (Polyhedron Promoter and stippled arrow on plasmid) for pJVP10Z are also shown.

hrPDE-IV Activity assay and assay for hrPDE-IV inhibition

The following assay was employed to assess the ability of the compounds of the invention to inhibit hrPDE IV. Baculovirus expressed hrPDE-IV was assayed using a modified version of the coupled enzyme protocol described by Kono. See Kono, T. (1984) in Methods in Diabetes Research, Vol. I (Larner, J., and Pehl, S. L., eds.), pp. 83–91, John Wiley & Sons, New York. In this assay, hrPDE-IV activity converts [$^3$H]cAMP to [$^3$H]AMP in proportion to the amount of hrPDE-IV activity present. The [$^3$H]AMP is then completely converted to [$^3$H]adenosine by excess 5'-nucleotidase. The amount of [$^3$H]adenosine liberated is therefore directly proporational to the hrPDE-IV activity. [$^{14}$C]adenosine is used as an internal control. The assay is performed at 30° C. in a 50 µl reaction mixture containing: 1 mM Tris-HCl (pH 7.5), 1 mM MgCl$_2$, 0.1 mM EDTA, 0.33 µg/µl BSA, 0.5 µg 5'-nucleotidase, 0.1 µM $^3$H-cAMP, 1 µM $^{14}$C-Ad, hrPDE IV stock solution, and the desired concentration of test compound. The PDE IV reaction was stopped with 200 µl of a slurry containing 50% Sephadex A-25 and 5 mM CAPS (pH 10). The mixture of [$^3$H]adenosine and [$^{14}$C]adenosine was eluted batchwise from the slurry, the amount of radioactivity is determined and the hrPDE-IV activity is calculated.

The Ki's of compounds set forth in the Examples were determined by measuring the inhibition of cAMP hydrolysis as a function of the concentration of the test compound over the range of 0 to 100 µM. The Ki's of the compounds tested in the aforementioned assay ranged from about 4 nM to about 20 µM.

Assay for binding to hrPDE-IV

The binding of [$^3$H]rolipram to hrPDE-IV was assessed using a modified version of the protocol described by Schneider, et al (see Schneider, et al, Eur J Pharmacol 127:105, 1986). hrPDE IV is incubated with [$^3$H]rolipram (e-9M final) and test compounds (e-11 thru e-4M) in a volume of 1.0 mL containing (mM): NaCl (100), Tris-HCl (25), MgCl2 (10), CaCl2 (1) dithiothreitol (1) and BSA (0.25%) pH 7.4. Reaction termination: brain homogenate-after 60 min at room temperature the reaction mixture is filtered onto polyethyleneimine treated (0.3%, >3 hours) glass fiber filters; recombinant PDE IV-after 60 min on ice, hydroxyapatite is added (final HAP is 2.5% w/v) with vigorous mixing to adsorb the ligand/receptor complex prior to filtration onto glass fiber filters as described above. Radioactivity is quantitated by liquid scintillation counting. IC50 values for test compound competition for rolipram binding are estimated from concentration/response curves and converted to Ki values using the Cheng-Prusoff correction. The Ki's of the compounds tested in the aforementioned assay ranged from about 1 nM to about 20 µM.

Assay for inhibition of LPS-induced TNFα production

In order to assess the ability of a compound to reduce TNFα secretion in elicited mouse peritoneal macrophages, the following protocol was employed. It will be appreciated by those skilled in the art that previous studies have demonstrated that incubation of human or mouse monocytes with cAMP elevating agents, such as prostaglandin E$_2$ (PGE$_2$), forskolin or dbcAMP, inhibit lipopolysaccharide (LPS)-induced secretion of TNFα. (See Scales, W. E., S. W. Chensue, I. Otterness and S. L. Kunkel, 1989, Regulation of monokine gene expression: Prostaglandin E$_2$ suppresses tumor necrosis factor but not interleukin-1a or b-mRNA and cell-associated bioactivity, J. Leukocyte Biology 45:416–421.). (See also Renz, H., J-H. Gong, A. Schmidt, M. Nain and Diethard Gemsa, 1988, Release of tumor necrosis factor-a from macrophages. Enhancement and suppression are dose-dependently regulated by prostaglandin E$_2$ and cyclic nucleotides, J. Immunol. 1 41:2388–2393). Accordingly, preliminary experiments were performed to demonstrate that rolipram, a type IV specific phosphodiesterase inhibitor, inhibited LPS induced TNFα secretion from murine macrophages. (See Noel, L. S., M. Verghese, K. M. Connelly, L. J. Sekut and S. A. Stimpson, 1992, Type IV-specific phosphodiesterase (PDE) inhibitors suppress murine TNFα expression in vitro and in vivo-(abstract)—6$^{th}$ International Conference, Inflammation Research Association). TNFα secretion from murine elicited peritoneal macrophages was used as a readout for a compound's ability to raise cAMP, and/or inhibit phosphodiesterase within a cell.

Mice (female C3H mice, 15–20 gm body weight) were injected intraperitoneally with 2 mL of 5 mM sodium periodate solution. Five days later, animals were sacrificed under CO$_2$ and the cells recovered as follows. Ten mL of cold phosphate buffered saline (PBS) was injected into the peritoneal cavity, the abdomen massaged, and fluid recovered. Cells were washed 2 times with cold PBS containing 5 mM EDTA, centrifuged at 1100×g for 7 min and resuspended in warm RPMI medium (GIBCO RPMI Medium 1604 containing 25 mM HEPES, L-glutamine, 1% Hyclone fetal bovine serum, penicillin and streptomycin) at a concentration of $5\times10^5$ cells/mL. One mL of cells was placed into each well of a 24-well tissue culture plate. Cells were incubated 2 to 2.5 hours at 37° C. under 7% $CO_2$. Wells were gently washed 2 times with warm PBS, without EDTA. The remaining, adherent cells are approximately 95% macrophages. Compounds were dissolved in dimethylsulfoxide (DMSO) to a concentration of 10 mM. These stock solutions were then diluted into RPMI medium. Compounds were added to wells approximately 10 min. before LPS addition (the time necessary to prepare and add LPS). DMSO similarly diluted in medium was used as a negative control. Cells were cultured 16 hours at 37° C., 7% $CO_2$. Following incubation, 0.7 mL of supernatant was removed to polypropylene tubes for $TNF\alpha$ measurement. $TNF\alpha$ protein in the supernatant fluids was measured using a commercially available enzyme-linked immunosorbant assay (ELISA) (Genzyme).

Assay for inhibition of serum $TNF\alpha$ levels in mammals

In order to assess the ability of a compound to reduce serum $TNF\alpha$ levels in mammals, the following protocol was employed. It will be appreciated by those skilled in the art that previous studies have demonstrated that incubation of LPS-activated human monocytes with agents that can elevate cAMP, like PGE2, forskolin and dbcAMP, inhibited secretion of $TNF\alpha$. PDE-IV inhibitors like rolipram, which also elevate cAMP, have been found to inhibit serum $TNF\alpha$ as well. Rolipram has also been found to inhibit secretion of $TNF\alpha$ from LPS-activated mouse macrophages. Accordingly, in vivo efficacy of a PDE-IV reducing compound was shown by dosing with compound and measuring reduction of serum $TNF\alpha$ levels in LPS-injected mice. Female C3H mice, 20–25 gm body weight were fasted overnight and dosed orally with test compound in appropriate vehicle 30 minutes before LPS injection. Five μg of LPS was then injected intraperitoneally into the mice. Exactly 90 minutes after LPS injection, mice were bled from the heart. Blood was allowed to clot overnight at 4° C. Samples were centrifuged for 10 minutes in a micro centrifuge and the serum removed and stored at −20° C. until analysis. Serum levels of $TNF\alpha$ were subsequently measured using a commercially available ELISA kit (Genzyme) following the protocol enclosed in the kit. The percent of inhibition of serum $TNF\alpha$ levels caused by the compound was determined relative to serum $TNF\alpha$ levels in control mice receiving vehicle alone.

Assay for inhibition of experimental arthritis in rats

The ability of a compound to inhibit experimental arthritis in rats was determined using the reactivation of peptidoglycan-polysaccharide (PG-PS)-induced monarthritis model (see Stimpson, S. A., and J. H. Schwab, 1989, Chronic remittent erosive arthritis induced by bacterial peptidoglycan-polysaccaride structures, as referenced in Pharmacological Methods in the Control of Inflammation, J. Chang and A. S. Lewis, eds., Alan R. Liss, Inc., New York, pp. 381–394). The following protocol was employed. PG-PS was purified from group A streptococcal cell walls by exhaustive extraction with detergents, sonicated and fractionated by differential centrifugation. PG-PS fragments sedimenting at 100,000×g, but not at 10,000×g, were used (PG-PS 100P fraction). The rhamnose content of the PG-PS 100P was determined by standard colorimetric assay for methylpentose (see Dische and Shettles, J Biol Chem 175:590, 1948). All PG-PS doses were based on rhamnose equivalent. Female Lewis rats (ca. 150 g) were primed in the right ankle with an intraarticular injection of 2.5 μg PG-PS 100P. This causes an acute inflammatory reaction which peaks within 24 hours and gradually wanes, leaving a mild chronic inflammation of the ankle. Two weeks later (day 0), rats are injected intravenously with 150 μg PG-PS 100P. This induces a reactivation of arthritis in the primed ankles which peaks in severity in 48 to 72 hours. This reactivation of arthritis is quantified by determining the increase in swelling of the ankle joint immediately before to 48 hours after the intravenous PG-PS injection. Compounds in an appropriate vehicle (usually methyl cellulose or cottonseed oil) are administered orally at −1, 6,24 and 30 hours relative to the intravenous PG-PS injection. Joint swelling is measured at 48 hours and % inhibition caused by the comound is determined relative to control arthritic rats which were treated with vehicle alone.

We claim:

1. A compound of Formula (I)

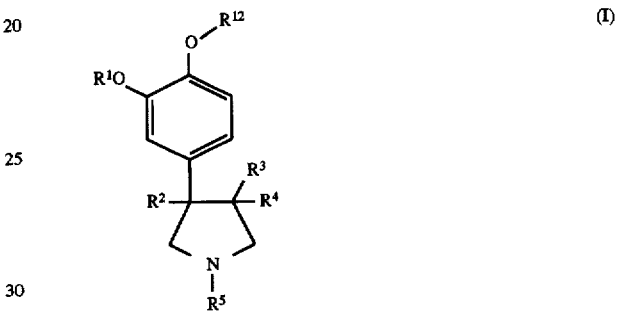

wherein:

$R^1$ is alkyl, haloalkyl, cycloalkyl, bridged polycycloalkyl, aryl, aralkyl, heteroaralkyl, aryloxyalkyl or a 5 to 6-membered heterocyclic aromatic group optionally fused to a benzene ring and optionally substituted with one or more substituents selected from halogen, alkyl, hydroxy, alkoxy, haloalkyl, nitro, amino, acylamino, alkylthio, alkylsulfinyl and alkylsulfonyl;

$R^2$ is H, alkyl, haloalkyl, cycloalkyl, aryl, —CO-alkyl, —CO-cycloalkyl, —CO-aryl, —COO-alkyl, —COO-cycloalkyl, —COO-aryl, $CH_2OH$, $CH_2$—O-alkyl, —CHO, —CN, —$NO_2$ or $SO_2R^{10}$;

$R^3$ is —CO-alkyl, —CO-haloalkyl, —CO-cycloalkyl, —COO-alkyl, —COO-cycloalkyl, —COOH, —CO-aryl, —$CONR^6R^7$, —$CH_2OH$, —$CH_2$O-alkyl, —CHO, —CN, —$NO_2$, —$NR^8COR^9$, —$NR^8SO_2R^{10}$ or —$SO_2R^{10}$;

$R^4$ is H, alkyl, haloalkyl, cycloalkyl, —CO-alkyl, —CO-haloalkyl, —CO-cycloalkyl, —COO-alkyl, —COO-cycloalkyl, —COOH, —CO-aryl, —$CONR^6R^7$, —CN, —CHO or $SO_2R^{10}$;

$R^5$ is —CN or —C(X)—$R^{11}$ or $SO_2R^{10}$;

$R^6$ and $R^7$ are independently selected from H, alkyl, cycloalkyl, aryl or aralkyl or $R^6$ and $R^7$ together form a 4- to 7-membered heterocyclic or carbocyclic ring;

$R^8$ is H, alkyl or cycloalkyl;

$R^9$ is alkyl, cycloalkyl, aryl, alkoxy, aralkoxy or —$NR^6R^7$;

$R^{10}$ is alkyl, cycloalkyl, trifluoromethyl, aryl, aralkyl or —$NR^6R^7$;

$R^{11}$ is H, alkyl, haloalkyl, cycloalkyl, aryl, aralkyl, $C_{1-6}$alkoxy, aralkoxy, aryloxy, —$NR^6R^7$ or a 5 to 6-membered heterocyclic aromatic group optionally fused to a benzene ring and optionally substituted with one or more substituents selected from halogen, alkyl, hydroxy, alkoxy, haloalkyl, nitro, amino, acylamino, alkylthio, alkylsulfinyl and alkylsulfonyl;

$R^{12}$ is $C_{1-3}$alkyl, cyclopropyl or $C_{1-3}$haloalkyl; and

X is O or S.

2. A compound according to claim 1 wherein $R^{12}$ is methyl.

3. A compound according to claim 2 wherein $R^5$ is —C(X)—$R^{11}$ and X is O.

4. A compound according to claim 3 wherein $R^1$ is selected from alkyl, cycloalkyl, bridged polycycloalkyl, aryl, aralkyl, heteroaralkyl or aryloxyalkyl.

5. A compound according to claim 4 wherein $R^1$ is selected from alkyl, cycloalkyl, bridged polycycloalkyl, aralkyl, heteroaralkyl or aryloxyalkyl.

6. A compound according to claim 5 wherein $R^1$ is selected from alkyl, cycloalkyl, bridged polycycloalkyl, aralkyl or aryloxyalkyl.

7. A compound according to claim 6 wherein $R^1$ is selected from alkyl, cycloalkyl, aralkyl or aryloxyalkyl.

8. A compound according to claim 3 wherein $R^2$ is selected from H, alkyl, cycloalkyl, —CO-alkyl, —CO-cycloalkyl, —CO-aryl, —COO-alkyl, —COO-cycloalkyl, —COO-aryl, —CN or $SO_2R^{10}$.

9. A compound according to claim 3 wherein $R^4$ is selected from H, alkyl, cycloalkyl, —CO-alkyl, —CO-cycloalkyl, —COO-alkyl, —COO-cycloalkyl, —COOH, —CONR$^6$R$^7$, —CN or $SO_2R^{10}$, provided that when $R^2$ is —COO-alkyl, —COOH, —CO-alkyl or —CO-aryl, $R^4$ is H.

10. A compound according to claim 3 wherein $R^9$ is selected from alkyl, cycloalkyl, alkoxy or aralkoxy.

11. A compound according to claim 1 wherein:

$R^1$ is selected from alkyl, cycloalkyl, aralkyl or aryloxyalkyl;

$R^2$ is selected from H, —COO-alkyl, —COO-cycloalkyl or $SO_2R^{10}$;

$R^4$ is selected from H, alkyl, cycloalkyl or $SO_2R^{10}$;

$R^5$ is —C(X)—$R^{11}$;

$R^6$ and $R^7$ are further independently selected from H or alkyl;

$R^8$ is H, alkyl or cycloalkyl;

$R^9$ is alkyl; and $R^{10}$ is selected from alkyl, trifluoromethyl or aryl;

$R^{11}$ is selected from H, alkyl, heteroaryl, $C_{1-6}$alkoxy, aralkoxy or —NR$^6$R$^7$;

$R^{12}$ is methyl; and

X is O.

12. A compound according to claim 1 wherein the compound is selected from one of the following:

cis-3-(3-cyclopentoxy-4-methoxyphenyl)-1-(1,1-dimethylethoxycarbonyl)-4-(methoxycarbonyl)pyrrolidine;

trans-3-(3-cyclopentoxy-4-methoxyphenyl)-1-(1,1-dimethylethoxycarbonyl)-4-(methoxycarbonyl)pyrrolidine;

trans-3-methoxycarbonyl-1-(1,1-dimethylethoxycarbonyl)-4-[3-(3-phenoxypropoxy)-4-methoxyphenyl]pyrrolidine;

trans-3-(3,4-dimethoxyphenyl)-1-(1,1-dimethylethoxycarbonyl)-4-(methoxycarbonyl)pyrrolidine;

3-(3-cyclopentoxy-4-methoxyphenyl)-1-(1,1-dimethylethoxycarbonyl)-3-(methoxycarbonyl)pyrrolidine;

trans-3-(3-cyclopentoxy-4-methoxyphenyl)-1-(1,1-dimethylethoxycarbonyl)-4-(hydroxymethyl)pyrrolidine;

trans-3-(3-cyclopentoxy-4-methoxyphenyl)-4-hydroxymethyl-1-(methoxycarbonyl)pyrrolidine;

trans-1-aminocarbonyl-3-(3-cyclopentoxy-4-methoxyphenyl)-4-(methoxycarbonyl)pyrrolidine;

cis-1-aminocarbonyl-3-(3-cyclopentoxy-4-methoxyphenyl)-4-(methoxycarbonyl)pyrrolidine;

trans-1-methoxycarbonyl-3-methoxycarbonyl-4-(3-phenylmethoxy-4-methoxyphenyl)pyrrolidine;

3-(3-cyclopentoxy-4-methoxyphenyl)-1-methoxycarbonyl-4-methyl-4-(methylcarbonyl)pyrrolidine;

trans-3-(3-cyclopentoxy-4-methoxyphenyl)-4-(1,1-dimethylethoxycarbonyl)-1-(methoxycarbonyl)pyrrolidine;

3-(3-cyclopentoxy-4-methoxyphenyl)-4-(1,1-dimethylethoxycarbonyl)-1-methoxycarbonyl-4-methylpyrrolidine;

trans-3-(3-cyclopentoxy-4-methoxyphenyl)-4-ethylcarbonyl-1-(methoxycarbonyl)pyrrolidine;

trans-1-methoxycarbonyl-3-nitro-4-[3-(3-phenoxypropoxy)-4-methoxyphenyl]pyrrolidine;

trans-3-cyano-4-(3-cyclopentoxy-4-methoxyphenyl)-1-(methoxycarbonyl)pyrrolidine;

trans-3-(3-cyclopentoxy-4-methoxyphenyl)-1-methoxycarbonyl-4-nitropyrrolidine;

trans-3-(3-cyclopentoxy-4-methoxyphenyl)-1-methoxycarbonyl-4-(methylcarbonyl)pyrrolidine;

trans-3-(3-cyclopentoxy-4-methoxyphenyl)-1-methoxycarbonyl-4-(phenylcarbonyl)pyrrolidine;

trans-1-methoxycarbonyl-3-methoxycarbonyl-4-[3-(3-phenoxypropoxy)-4-methoxyphenyl]pyrrolidine;

3-(3-cyclopentoxy-4-methoxyphenyl)-4-ethoxycarbonyl-1-methoxycarbonyl-4-methylpyrrolidine;

3-(3-cyclopentoxy-4-methoxyphenyl)-4-methoxycarbonyl-1-methoxycarbonyl-4-methylpyrrolidine;

trans-3-(3-cyclopentoxy-4-methoxyphenyl)-1-methoxycarbonyl-4-(methylcarbonyl)pyrrolidine;

trans-3-(3-cyclopentoxy-4-methoxyphenyl)-4-methoxycarbonyl-1-(methylcarbonyl)pyrrolidine;

trans-3-(3-cyclopentoxy-4-methoxyphenyl)-1-ethylcarbonyl-4-(methoxycarbonyl)pyrrolidine;

trans-3-(3-cyclopentoxy-4-methoxyphenyl)-1-(1-imidazolylcarbonyl)-4-(methoxycarbonyl)pyrrolidine;

trans-3-(3-cyclopentoxy-4-methoxyphenyl)-1-formyl-4-(methoxycarbonyl)pyrrolidine;

trans-1-formyl-3-methoxycarbonyl-4-[3-(3-phenoxypropoxy)-4-methoxyphenyl]pyrrolidine;

trans-3-(3-cyclopentoxy-4-methoxyphenyl)-1-methoxycarbonyl-4-(1-methylethoxycarbonyl)pyrrolidine;

trans-3-(3-cyclopentoxy-4-methoxyphenyl)-4-ethoxycarbonyl-1-(methoxycarbonyl)pyrrolidine;

trans-3-carboxy-4-(3-cyclopentoxy-4-methoxyphenyl)-1-(1,1-dimethylethoxycarbonyl)pyrrolidine;

trans-3-carboxy-4-(3-cyclopentoxy-4-methoxyphenyl)-1-methoxycarbonyl)pyrrolidine;

trans-3-carboxy-4-(3-cyclopentoxy-4-methoxyphenyl)-1-(phenylmethoxycarbonyl)pyrrolidine;

trans-3-carboxy-4-(3-cyclopentoxy-4-methoxyphenyl)-1-(1-methylethoxycarbonyl)pyrrolidine;

trans-3-carboxy-1-(methoxycarbonyl)-4-[3-(3-phenoxypropoxy)-4-methoxyphenyl]pyrrolidine;

trans-3-carboxy-4-(3-cyclopentoxy-4-methoxyphenyl)-1-formylpyrrolidine;

trans-1-aminocarbonyl-3-carboxy-4-(3-cyclopentoxy-4-methoxyphenyl)pyrrolidine;

trans-3-aminocarbonyl-4-(3-cyclopentoxy-4-methoxyphenyl)-1-(methoxycarbonyl)pyrrolidine;

trans-3-aminocarbonyl-4-(3-cyclopentoxy-4-methoxyphenyl)-1-(1,1-dimethylethoxycarbonyl)pyrrolidine;

trans-3-(3-cyclopentoxy-4-methoxyphenyl)-1-(1,1-dimethylethoxycarbonyl)-4-[(N-phenylmethyl)aminocarbonyl]pyrrolidine;

trans-3-(3-cyclopentoxy-4-methoxyphenyl)-4-N-(1,1-dimethylethoxycarbonyl)-1-(1,1-dimethylethoxycarbonyl)pyrrolidine;

trans-3-(3-cyclopentoxy-4-methoxyphenyl)-4-N-(1,1-dimethylethoxycarbonyl)-1-(methoxycarbonyl)pyrrolidine;

trans-3-(3-cyclopentoxy-4-methoxyphenyl)-4-N-(1,1-dimethylethoxycarbonyl)-1-(phenylmethoxycarbonyl)pyrrolidine;

trans-3-(3-cyclopentoxy-4-methoxyphenyl)-4-[N-(1,1-dimethylethoxycarbonyl)-N-methyl]-1-(phenylmethoxycarbonyl)pyrrolidine;

trans-3-(3-cyclopentoxy-4-methoxyphenyl)-4-N-(methylsulfonyl)-1-(phenylmethoxycarbonyl)pyrrolidine;

trans-3-(3-cyclopentoxy-4-methoxyphenyl)-1-(phenylmethoxycarbonyl)-4-N-(trifluoromethylsulfonyl)pyrrolidine;

trans-3-(3-cyclopentoxy-4-methoxyphenyl)-4-N-(phenylsulfonyl)-1-(phenylmethoxycarbonyl)pyrrolidine;

trans-3-(3-cyclopentoxy-4-methoxyphenyl)-1-methoxycarbonyl-4-N-methoxycarbonyl)pyrrolidine;

trans-1-aminocarbonyl-3-(3-cyclopentoxy-4-methoxyphenyl)-4-N-(1,1-dimethylethoxycarbonyl)pyrrolidine;

trans-1-aminothiocarbonyl-3-(3-cyclopentoxy-4-methoxyphenyl)-4-(methoxycarbonyl)pyrrolidine;

trans-1-cyano-3-(3-cyclopentoxy-4-methoxyphenyl)-4-(methoxycarbonyl)pyrrolidine;

trans-3-(3-cyclopentoxy-4-methoxyphenyl)-4-methoxycarbonyl-1-(phenylmethoxycarbonyl)pyrrolidine;

trans-3-(3-cyclopentoxy-4-methoxyphenyl)-4-methoxycarbonyl-1-(methylethoxycarbonyl)pyrrolidine;

3-(3-cyclopentoxy-4-methoxyphenyl)-1-(1,1-dimethylethoxycarbonyl)-4-methoxycarbonyl-4-methylpyrrolidine; and trans-3-(3-cyclopentoxy-4-methoxyphenyl)-1-methoxycarbonyl-4-(methoxymethyl)pyrrolidine.

13. A method of treating a mammal for inflammatory diseases comprising administering to said mammal an effective amount of a compound according to claim 1.

14. A method of treating a mammal for osteoarthritis and rheumatoid arthritis which comprises administering to said mammal an effective amount of a compound according to claim 1.

15. A method of treating a mammal for sepsis, septic shock, endotoxic shock and gram negative or gram positive sepsis or toxic shock syndrome which comprises administering to said mammal an effective amount of a compound according to claim 1.

16. A method of treating a mammal for adult respiratory distress syndrome, chronic pulmonary inflammatory disease, asthma, silicosis or pulmonary sacroidosis which comprises administering to said mammal an effective amount of a compound according to claim 1.

17. A method according to claim 16 comprising selectively treating said mammal for asthma.

18. A method of treating a mammal for lupus erythematosus, inflammatory bowel disease, Crohn's disease, ulcerative colitis and transplant rejection which comprises administering to said mammal an effective amount of a compound according to claim 1.

19. A method of treating a mammal for diabetes insipidus which comprises administering to said mammal an effective amount of a compound according to claim 1.

20. A method of treating a mammal for osteoporosis which comprises administering to said mammal an effective amount of a compound according to claim 1.

21. A method of treating a mammal for AIDS and ARC which comprises administering to said mammal an effective amount of a compound according to claim 1.

22. A method for suppressing inflammatory cell activation in a mammal comprising administering to said mammal an effective amount of a compound according to claim 1.

23. A method of reducing TNF levels in a mammal comprising administering to said mammal an effective amount of a compound according to claim 1.

24. A method of inhibiting phosphodiesterase Type IV function in a mammal comprising administering to said mammal an effective amount of a compound according to claim 1.

25. A method for modulating cAMP levels in a mammal comprising administering to said mammal an effective amount of a compound according to claim 1.

26. A pharmaceutical composition comprising a compound of claim 1 and a pharmaceutically acceptible carrier.

* * * * *

UNITED STATES PATENT AND TRADEMARK OFFICE
CERTIFICATE OF CORRECTION

PATENT NO. : 5,665,754

DATED : September 9, 1997

INVENTOR(S) : Paul L. Feldman et al.

It is certified that error appears in the above-identified patent and that said Letters Patent is hereby corrected as shown below:

Column 2, line 27, "graff" should be --graft--.

Column 2, line 50, "anglogenesis" should be --angiogenesis--.

Column 4, line 28, delete the second "cyclobutyl,".

Column 4, line 43, "4-nitropohenyl," should be -- 4-nitrophenyl, --.

Column 13, line 9, "multiplat;" should be --multiplet;--

Column 15, last line, "(triphenylphospohoranylidene)" should be --(triphenylphosphoranylidene)--.

Column 20, line 4, "dimethytethoxycarbonyl" should be --dimethylethoxycarbonyl--.

Column 26, line 29, "(1-(methylethoxycarbonyl)" should be --(1-methylethoxycarbonyl)--.

Column 26, line 35, before "drops" insert --2--.

Column 27, line 55, "[8" should be --[3--.

Column 28, line 31, " -l- " should be -- -1- --.

UNITED STATES PATENT AND TRADEMARK OFFICE
CERTIFICATE OF CORRECTION

PATENT NO. : 5,665,754
DATED : September 9, 1997
INVENTOR(S) : Paul L. Feldman et al.

It is certified that error appears in the above-identified patent and that said Letters Patent is hereby corrected as shown below:

Column 29, line 38, "Found: 0," should be --Found: C,--.

Column 29, last line, "-$CO_{CH2}$-" should be -- -$CO_2CH_2$- --.

Column 34, line 55, "constutuents" should be --constituents--.

Column 35, line 5, "leukocyteisis" should be --leukocytoisis--.

Column 35, line 19, "fibreblasts," should be --fibroblasts,--.

Column 35, line 32, "in vive" should be --in vivo--.

Column 35, line 37, "in vive" should be --in vivo--.

Column 38, line 20, "eDNA" should be --cDNA--.

Column 38, line 31, "eDNA" should be --cDNA--.

Column 39, line 11, "orgin" should be --origin--.

Column 39, line 59, "proporational" should be --proportional--.

UNITED STATES PATENT AND TRADEMARK OFFICE
CERTIFICATE OF CORRECTION

PATENT NO. : 5,665,754
DATED : September 9, 1997
INVENTOR(S) : Paul L. Feldman et al.

It is certified that error appears in the above-identified patent and that said Letters Patent is hereby corrected as shown below:

Column 40, line 47, "1 41:2388-2393)" should be --141:2388-2393)--

Column 41, line 55, "polysaccaride" should be --polysaccharide--.

Column 42, line 14, "comound" should be --compound--.

Column 43, line 40, delete "further".

Signed and Sealed this

Eleventh Day of August 1998

Attest:

BRUCE LEHMAN

Attesting Officer

Commissioner of Patents and Trademarks